US006573069B1

(12) United States Patent
Holloway et al.

(10) Patent No.: US 6,573,069 B1
(45) Date of Patent: Jun. 3, 2003

(54) CRIB PROTEIN ZMSE1

(75) Inventors: James L. Holloway, Seattle, WA (US); Zeren Gao, Redmond, WA (US); Theodore E. Whitmore, Redmond, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/710,794

(22) Filed: Nov. 9, 2000

Related U.S. Application Data

(60) Provisional application No. 60/164,685, filed on Nov. 10, 1999.

(51) Int. Cl.$^7$ .............................................. C12P 21/06
(52) U.S. Cl. .................. 435/69.1; 435/243; 435/320.1; 435/325; 435/348; 435/349; 435/352; 435/410; 435/455; 435/468; 435/471; 536/23.5; 536/23.4
(58) Field of Search ........................ 424/93.2; 530/350; 536/23.1, 23.5, 23.4; 435/69.1, 320.1, 325, 455, 352, 468, 471, 348, 349, 410, 243

(56) References Cited

FOREIGN PATENT DOCUMENTS

WO         99/51727        10/1999

OTHER PUBLICATIONS

CC Linder, Lab Animal, "The Influence of Genetic Background on Spontaneous and Genetically Engineered Mouse Models of Complex Diseases," May 2001, vol. 30, No. 5, pp. 34–39.*
Hirsch, DS. et al., EMBL Database, Georgetown University Medical Center, Mar. 11, 1999: AF099664.
Osada, N et al., *J. Human Genetics* 45:374–377, 2000.
Joberty, G et al., *Mol. and Cell. Biol.* 19:6585–6597, 1999.
Burbelo, P.D. et al., *Proc. Nat'l. Acad. Sci.* 96:9083–9088, 1999.
Bahou et al., *J Biol. Chem.* 267:13986–13992, 1992.
Burbelo, P.D. et al.,*J. Biol. Chem.* 270:29071–29074, 1995.
Bahou et al., *J. Biol. Chem.* 267:13986–13992, 1992.
Zohn, I.M. et al., *Oncogene* 17:1415–1438, 1998.
Adams, MD. et al., Genbank Database, The Institute for Genomic Research, 1993: EST25485.
Wilson RK. et al., Genbank Database, Wash. U. School of Medicine, 1995: EST274424.
Wilson RK. et al., Genbank Database, Wash. U. School of Medicine, 1995: EST626917.
Marra, M. et al., Genbank Database, The WashU–HHMI Mouse EST Project, 1996: EST1166173.
Adams, MD. et al., Genbank Database, The Institute for Genomic Research, 1996: G19982.
Marra, M. et al., Genbank Database, The WashU–HHMI Mouse EST Project, 1996: EST1874398.
Incyte Pharmaceuticals, Inc. clone, 1996: INC1629555.
Incyte Pharmaceuticals, Inc. clone, 1996: INC1686839.
Incyte Pharmaceuticals, Inc. clone, 1996: INC1501852.
Incyte Pharmaceuticals, Inc. clone, 1996: INC1859584.
Incyte Pharmaceuticals, Inc. clone, 1996: INC1916576.
Incyte Pharmaceuticals, Inc. clone, 1996: INC1932856.
Incyte Pharmaceuticals, Inc. clone, 1997: INC2516458.
Incyte Pharmaceuticals, Inc. clone, 1997: INC2737451.
Incyte Pharmaceuticals, Inc. clone, 1997: INC2606509.
Incyte Pharmaceuticals, Inc. clone, 1997: LIN1859584F6.
Incyte Pharmaceuticals, Inc. clone, 1997: INC2744649.
Incyte Pharmaceuticals, Inc. clone, 1997: INC2817289.
Incyte Pharmaceuticals, Inc. clone, 1997: INC2825493.
Incyte Pharmaceuticals, Inc. clone, 1997: INC3151224.
TIGR Tentative Human Consensus, 1997: THC_AA013011.
TIGR Tentative Human Consensus, 1997: : THC_EST04320.
TIGR Tentative Human Consensus, 1997: THC_H14486.
Incyte Pharmaceuticals, Inc. clone, 1997: INC2466008.
Incyte Pharmaceuticals, Inc. clone, 1997: INC3438506.
Incyte Pharmaceuticals, Inc. clone, 1997: INC3507143.
Incyte Pharmaceuticals, Inc. clone, 1997: INC3574066.
Incyte Pharmaceuticals, Inc. clone, 1997: INC3768324.
Incyte Pharmaceuticals, Inc. clone, 1997: INC4079786.
Incyte Pharmaceuticals, Inc. clone, 1997: INC3940912.
Incyte Pharmaceuticals, Inc. clone, 1998: INC4251793.
Incyte Pharmaceuticals, Inc. clone, 1998: INC4182093.
Incyte Pharmaceuticals, Inc. clone, 1998: INC3791270.
Incyte Pharmaceuticals, Inc. clone, 1998: INC4181450.
Incyte Pharmaceuticals, Inc. clone, 1998: INC802504.
Incyte Pharmaceuticals, Inc. Library, 1996: COLNPOT01.
Incyte Pharmaceuticals, Inc. Library, 1996: PROSNOT15.
Incyte Pharmaceuticals, Inc. Library, 1996: SINTBST01.
Incyte Pharmaceuticals, Inc. Library, 1996: PROSNOT18.
Incyte Pharmaceuticals, Inc. Library, 1996: PROSNOT06.
Incyte Pharmaceuticals, Inc. Library, 1996: COLNNOT16.
Incyte Pharmaceuticals, Inc. Library, 1997: LIVRTUT04.
Incyte Pharmaceuticals, Inc. Library, 1997: OVARNOT09.
Incyte Pharmaceuticals, Inc. Library, 1997: LUNGTUT07.
Incyte Pharmaceuticals, Inc. Library, 1997: BRSTTUT14.
Incyte Pharmaceuticals, Inc. Library, 1997: BRSTNOT14.
Incyte Pharmaceuticals, Inc. Library, 1997: ADRETUT06.
Incyte Pharmaceuticals, Inc. Library, 1997: ADRENON04.

(List continued on next page.)

*Primary Examiner*—Scott D. Priebe
*Assistant Examiner*—Brian Whiteman
(74) *Attorney, Agent, or Firm*—Jennifer K. Johnson

(57) ABSTRACT

The present invention relates to polynucleotide and polypeptide molecules for zmse1, a novel human CRIB protein. The polypeptides, and polynucleotides encoding them, may be used for detecting human chromosomal abnormalities and cancers. The present invention also includes antibodies to the zmse1 polypeptides.

14 Claims, 10 Drawing Sheets

OTHER PUBLICATIONS

Incyte Pharmaceuticals, Inc. Library, 1997: THYRNOT08.
Incyte Pharmaceuticals, Inc. Library, 1997: PENCNOT06.
Incyte Pharmaceuticals, Inc. Library, 1997: CONCNOT01.
Incyte Pharmaceuticals, Inc. Library, 1997: BRONNOT01.
Incyte Pharmaceuticals, Inc. Library, 1997: BRSTNOT24.
Incyte Pharmaceuticals, Inc. Library, 1997: CONFNOT02.
Incyte Pharmaceuticals, Inc. Library, 1997: SCORNOT04.
Incyte Pharmaceuticals, Inc. Library, 1998: BRADDIR01.
Incyte Pharmaceuticals, Inc. Library, 1998: BRAUNOT01.
Incyte Pharmaceuticals, Inc. Library, 1998: BRSTNOT28.
Incyte Pharmaceuticals, Inc. Library, 1998: SINITUT03.
Incyte Pharmaceuticals, Inc. Library, 1998: BRAVTXT05.

* cited by examiner

| | | | |
|---|---|---|---|
| 42 | 0.67 | R | ======= |
| 43 | 0.83 | A | ======== |
| 44 | 0.42 | G | ==== |
| 45 | -0.08 | = D | |
| 46 | 0.50 | A | ===== |
| 47 | 0.43 | F | ==== |
| 48 | -0.02 | G | |
| 49 | -0.35 | ==== D | |
| 50 | -0.23 | == T | |
| 51 | -0.20 | == S | |
| 52 | -0.65 | ======= F | |
| 53 | -0.08 | = L | |
| 54 | -0.22 | == N | |
| 55 | 0.20 | S | == |
| 56 | 1.00 | K | ========== |
| 57 | 0.97 | A | ========== |
| 58 | 1.42 | G | ============== |
| 59 | 0.92 | E | ========= |
| 60 | 1.50 | P | =============== |
| 61 | 1.55 | D | ================ |
| 62 | 0.75 | G | ======== |
| 63 | 1.25 | E | ============ |
| 64 | 1.25 | S | ============ |
| 65 | 1.28 | L | ============ |
| 66 | 0.78 | D | ======== |
| 67 | 0.78 | E | ======== |
| 68 | 1.13 | Q | =========== |
| 69 | 0.68 | P | ======== |
| 70 | 0.23 | S | == |
| 71 | 0.25 | S | === |
| 72 | 0.75 | S | ======== |
| 73 | 1.20 | S | ============ |
| 74 | 1.20 | S | =========== |
| 75 | 0.85 | K | ========== |
| 76 | 0.50 | R | ===== |
| 77 | 0.50 | S | ===== |
| 78 | 0.50 | L | ===== |
| 79 | 0.50 | L | ===== |
| 80 | 0.03 | S | |
| 81 | 0.83 | R | ======== |
| 82 | 1.13 | K | =========== |
| 83 | 1.13 | F | =========== |
| 84 | 1.13 | R | =========== |
| 85 | 1.13 | G | =========== |

| | | | |
|---|---|---|---|
| 130 | 0.90 | K | ========= |
| 131 | 1.48 | G | ============== |
| 132 | 0.68 | T | ======= |
| 133 | 0.18 | S | == |
| 134 | 0.68 | K | ======= |
| 135 | 0.80 | L | ======== |
| 136 | 0.45 | P | ===== |
| 137 | 0.00 | K | |
| 138 | 0.35 | S | ==== |
| 139 | 0.40 | L | ==== |
| 140 | -0.10 | = S | |
| 141 | -0.40 | ==== S | |
| 142 | 0.40 | S | ==== |
| 143 | 0.85 | P | ========= |
| 144 | 0.72 | V | ======= |
| 145 | 0.70 | K | ======= |
| 146 | 1.20 | K | ============ |
| 147 | 1.45 | A | ============== |
| 148 | 1.45 | N | ============== |
| 149 | 0.95 | D | ========== |
| 150 | 1.03 | G | ========== |
| 151 | 1.50 | E | =============== |
| 152 | 1.50 | G | =============== |
| 153 | 2.00 | G | ==================== |
| 154 | 1.42 | D | ============== |
| 155 | 1.42 | E | ============== |
| 156 | 1.35 | E | ============= |
| 157 | 1.35 | A | ============= |
| 158 | 1.35 | G | ============= |
| 159 | 0.77 | T | ======== |
| 160 | 0.60 | E | ====== |
| 161 | 0.60 | E | ====== |
| 162 | 1.17 | A | ============ |
| 163 | 1.17 | V | ============ |
| 164 | 0.70 | P | ======= |
| 165 | 0.78 | R | ======== |
| 166 | 0.95 | R | ========== |
| 167 | 0.87 | N | ========= |
| 168 | 0.37 | G | ==== |
| 169 | -0.13 | = A | |
| 170 | 0.15 | A | = |
| 171 | 0.20 | G | == |
| 172 | 0.28 | P | === |
| 173 | 0.87 | h | ========= |

| | | | |
|---|---|---|---|
| 262 | 0.15 | L | == |
| 263 | 0.65 | A | ======= |
| 264 | 0.65 | R | ======= |
| 265 | 1.45 | Q | ============== |
| 266 | 1.45 | E | ============== |
| 267 | 0.95 | G | ========== |
| 268 | 0.92 | K | ========= |
| 269 | 0.92 | A | ========= |
| 270 | 0.62 | G | ====== |
| 271 | 0.12 | P | = |
| 272 | 0.25 | D | === |
| 273 | -0.05 | L | |
| 274 | -0.05 | P | |
| 275 | -0.50 | ===== S | |
| 276 | -0.28 | === L | |
| 277 | -0.37 | ==== P | |
| 278 | -0.72 | ======= S | |
| 279 | 0.08 | H | = |
| 280 | 0.58 | A | ====== |
| 281 | 1.03 | L | ========== |
| 282 | 1.12 | E | =========== |
| 283 | 0.63 | D | ====== |
| 284 | 0.85 | E | ========= |
| 285 | 0.27 | G | === |
| 286 | -0.32 | === W | |
| 287 | -0.90 | ========= A | |
| 288 | -0.90 | ========= A | |
| 289 | -0.28 | === A | |
| 290 | -0.20 | == A | |
| 291 | -0.12 | = P | |
| 292 | 0.02 | S | |
| 293 | 0.02 | P | |
| 294 | 0.52 | G | ===== |
| 295 | 0.52 | S | ===== |
| 296 | 0.30 | A | === |
| 297 | 0.30 | R | === |
| 298 | 0.30 | S | === |
| 299 | 0.70 | M | ======= |
| 300 | 0.13 | G | = |
| 301 | 0.02 | S | |
| 302 | 0.73 | h | ======= |
| 303 | 1.23 | T | ============ |
| 304 | 1.23 | T | ============ |
| 305 | 0.97 | R | ========== |

FIG. 1G

| | | | |
|---|---|---|---|
| 306 | 1.08 | D | ========== |
| 307 | 0.85 | S | ========= |
| 308 | 0.40 | S | ==== |
| 309 | -0.67 | ======= S | |
| 310 | -0.88 | ========= L | |
| 311 | -1.00 | ========== S | |
| 312 | -1.62 | ================ S | |
| 313 | -1.32 | ============ C | |
| 314 | -1.67 | ================ T | |
| 315 | -1.40 | ============= S | |
| 316 | -0.73 | ======= G | |
| 317 | -0.17 | == I | |
| 318 | 0.90 | L | ========= |
| 319 | 0.95 | E | ========= |
| 320 | 1.25 | E | ============ |
| 321 | 1.47 | R | ============== |
| 322 | 0.55 | S | ====== |
| 323 | 0.55 | P | ====== |
| 324 | 0.05 | A | |
| 325 | 0.00 | F | |
| 326 | 0.50 | R | ===== |
| 327 | 1.08 | G | ========== |
| 328 | 1.42 | P | ============== |
| 329 | 1.42 | D | ============== |
| 330 | 1.33 | R | ============ |
| 331 | 1.25 | A | ============ |
| 332 | 0.50 | R | ===== |
| 333 | 0.05 | A | = |
| 334 | 0.63 | A | ====== |
| 335 | 0.17 | V | == |
| 336 | 0.25 | S | === |
| 337 | 0.83 | R | ======== |
| 338 | 1.58 | Q | =============== |
| 339 | 2.03 | P | ==================== |
| 340 | 1.12 | D | =========== |
| 341 | 1.13 | K | =========== |
| 342 | 0.72 | E | ======= |
| 343 | 0.00 | F | |
| 344 | 0.00 | S | |
| 345 | 0.00 | F | |
| 346 | 0.92 | M | ========= |
| 347 | 1.37 | D | ============== |
| 348 | 2.39 | E | ======================= |

FIG. 1H

```
           10        20        30        40        50        60
MUZMSE MPILKQLVSSSVNSKRRSRADLTAEMISAPLGDFRHTMHVGRAGDAFGDTSFLTSKAREA
       ::::::::::::.::::::::::::::::::::::::::::::::::::::::::::: :
zmse1  MPILKQLVSSSVHSKRRSRADLTAEMISAPLGDFRHTMHVGRAGDAFGDTSFLNSKAGEP
           10        20        30        40        50        60

70        80        90       100       110
MUZMSE DDESLDEQ--ASASKLSLLSRKFRGSKRSQSVTRGDREQRDMLGSLRDSALFVKNAMSLP
       : :::::::    .:.:: ::::::::::::::::::.:::::::::::::::::::::::
zmse1  DGESLDEQPSSSSSKRSLLSRKFRGSKRSQSVTRGEREQRDMLGSLRDSALFVKNAMSLP
           70        80        90       100       110       120

120       130       140       150             160       170
MUZMSE QLNEKEAAEKDSSKLPKSLSSSPVKKADARDGGPKS-------PHRNGATGPNSPDPLLD
       :::::::::::  .:::::::::::::::.  .:  ..        ::::..::::::::
zmse1  QLNEKEAAEKGTSKLPKSLSSSPVKKANDGEGGDEEAGTEEAVPRRNGAAGPHSPDPLLD
          130       140       150       160       170       180

180       190       200       210       220       230
MUZMSE EQAFGDLMDLPIMPKVSYGLKHAESILSFHIDLGPSMLGDVLSIMDKDQWGSEEEEEAGG
       ::::::::.:::.: ::.:::::::::.:::::::::::::::::::::.: :  :  ::
zmse1  EQAFGDLTDLPVVPKATYGLKHAESIMSFHIDLGPSMLGDVLSIMDKEEWDPEEGE--GG
             190       200       210       220       230

240       250       260       270       280       290
MUZMSE YRDKEGPS-SIVQAPPVLEVVPPLGRQESKASWDQASMLPPHAVEDDGWAVVAPSPSSAR
       :.   ::  . .:::::   .:::::.:.::  :  ::  ::.::.::::.:::::.:::
zmse1  YHGDEGAAGTITQAPPYAVAAPPLARQEGKAGPDLPS-LPSHALEDEGWAAAAPSPGSAR
           240       250       260       270       280       290

300       310       320       330       340
MUZMSE SVGSHTTRDSSSLSSYTSGVLEERSPAFRGPDRVAAAPPRQPDKEFCFMDEEEEDEIRV
       :.::::::::::::: .:::.:::::::::::::.  :: ::::::..:::::::::::
zmse1  SMGSHTTRDSSSLSSCTSGILEERSPAFRGPDRARAAVSRQPDKEFSFMDEEEEDEIRV
           300       310       320       330       340       350
```

FIG. 2

CRIB PROTEIN ZMSE1

REFERENCE TO RELATED APPLICATION

This application is related to Provisional Application No. 60/164,685, filed on Nov. 10, 1999. Under 35 U.S.C. §119 (e)(1), this application claims benefit of said Provisional Application.

BACKGROUND OF THE INVENTION

The Ras family of proteins is comprised of small GTPases that are subdivided into several sub-families known to be involved in diverse cellular actions, such as cell proliferation, differentiation and apoptosis. Moreover, Ras is a known oncogene, and the Ras protein is implicated in oncogenic cell transformation through complex signaling pathways that employ an increasing number of downstream effectors. Some of these effectors are included in Ras sub-families, such as, for example, the Rho subfamily of small GTPases.

The Rho family proteins are implicated in regulating diverse cellular processes as well. One prominent Rho activity comprises effecting actin cytoskeletal organization. Such activities include regulating cell shape, cell attachment and adhesion, cell motility and invasion, cell-cell interactions, cell proliferation, differentiation and apoptosis. For example, Rac1; RhoA and Cdc42 are all implicated in promoting cell motility and invasion. As such, these proteins may be involved in promoting motility, invasiveness and metastasis of tumor cells. In addition, disassembly of actin stress fibers is associated with malignant transformation. Moreover, another prominent and distinct Rho activity includes activation of signaling cascades that enhance gene expression through the induction of various transcription factors, resulting in cell proliferation, cell cycle progression, differentiation and apoptosis. For Example, the Rho proteins Rac1 and Cdc42 activate Jun $NH_2$-terminal kinases (JNKs), which in turn activate Jun, ATF-2 and Elk-1 nuclear transcription factors. Rho family proteins can also activate NFκB and SRF transcription factors. Virally transduced and mutated versions of cellular Fos, Jun, and NFκB were originally identified as potent retroviral oncogenes implicated in various tumors and cancerous states (Bishop, J. M., *Cell* 64:235–238, 1991). Thus, Rho family mediated changes in gene expression likely contribute to their proliferative actions, and play a role in cell transformation and cancer. Moreover, several Rho family proteins have been shown to be important for Ras transforming activity. For reference, see Zohn, I. M. et al., *Oncogene* 17:1415–1438, 1998; Maruta, H. et al., *Microsc. Res. Tech.* 47:61–66, 1999; Aspenstrom, P. *Exper. Cell. Res.* 246:20–25, 1999; Banyard, J. and Zetter, B. R., Cancer and *Metast. Rev.* 17:449–458, 1999; and, Michiels, F. and Collard, J. G., *Biochem Soc. Symp.* 65:125–146, 1999.

In addition, several effector proteins are known to bind Rho family members, such as Cdc42 and Rac. The effectors that bind Cdc42/Rac have a consensus binding motif designated the Cdc42/Rac Interactive Binding (CRIB) motif (Burbelo, P. D. et al., *J. Biol. Chem.* 270:29071–29074, 1995). These effectors show GTP-dependent interaction with Cdc42 and/or Rac1, and may or may not show kinase activity. For Example, the Cdc42 effector, MSE55 is a non-kinase effector that specifically binds Cdc42 in a GTP-dependent manner, is localized to membrane ruffles, and induces long actin-based protrusions or cellular extensions in fibroblast cells (Burbelo, P. D. et al., *Proc. Natl. Acad. Sci. USA* 96:9083–9088, 1999). For other references on Cdc2/Rac and their effects on membrane ruffling, actin stress fibers, lamellipodia and the like, see, for example, Ridley, A. J. et al., *Cell* 70:401–410, 1992; and Nobes, C. D., and Hall, A. *Cell* 81:53–62, 1995. Other CRIB proteins are implicated in human disease, such as the Wiskott-Aldrich Syndrome, which is an X-linked recessive disorder characterized by thrombocytopenia, recurrent infections due to defective T- and B-cell function, and eczema. The CRIB protein Wiskott-Aldrich Syndrome Protein (WASP) is mutated in this disease, and it is also a Cdc42 effector (Symons, M. et al., *Cell* 84:723–734, 1996). Because these CRIB proteins influence members of the Rho family of proteins, these effectors may also play a role in cell proliferation, transformation, motility and metastasis. For reference, see Zohn, I. M. et al., supra.

Considering the importance of this family of proteins, there is a continuing need to discover new Ras and Rho family members and their effector proteins that modulate the cytoskeleton, actin polymerization, cell motility and invasion, and the like, and affect proliferation, differentiation, transformation, metastasis and apoptotic pathways. The in vivo activities of both inducers and inhibitors of these pathways illustrate the enormous clinical potential of, and need for, such novel proteins, their agonists and antagonists, for example, in cancer therapy. The present invention addresses this need by providing such polypeptides for these and other uses that should be apparent to those skilled in the art from the teachings herein.

BRIEF DESCRIPTION OF THE DRAWINGS

FIGS. 1A–1I shows hydrophobicity plot of zmse1 using a Hopp/Woods hydrophilicity profile based on a sliding six-residue window, with buried G, S, and T residues and exposed H, Y, and W residues ignored.

FIG. 2 is an alignment of human zmse1 (zmse1) (SEQ ID NO:2), and mouse zmse1 (MUZMSE) (SEQ ID NO:5).

DESCRIPTION OF THE INVENTION

Figure 1A:
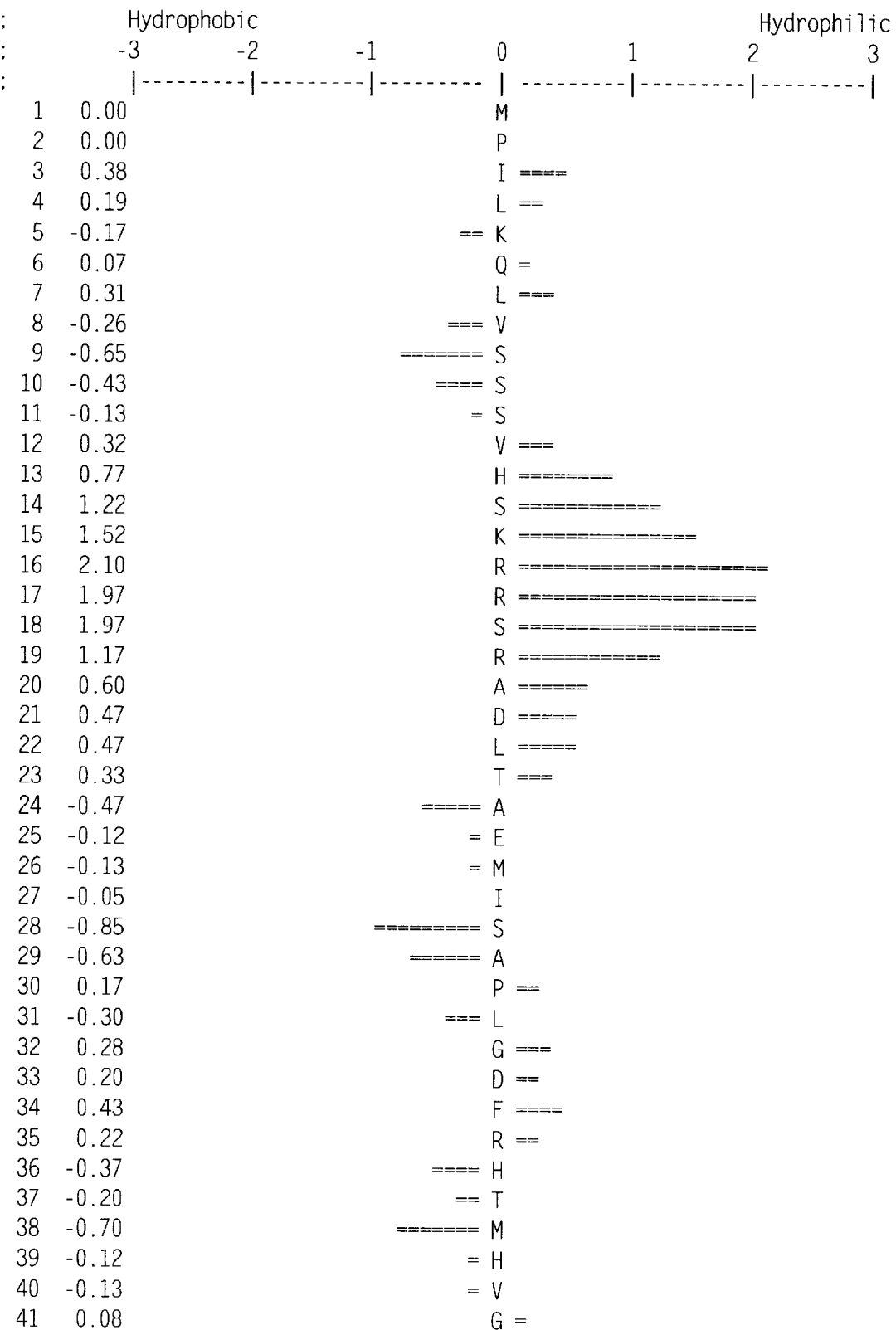

In one aspect, the present invention provides an isolated polynucleotide that encodes a zmse1 polypeptide comprising a sequence of amino acid residues that is at least 90% identical to an amino acid sequence selected from the group consisting of: (a) the amino acid sequence as shown in SEQ ID NO:2 from amino acid number 1 (Met), to amino acid number 147 (Ala); (b) the amino acid sequence as shown in SEQ ID NO:2 from amino acid number 148 (Asn), to amino acid number 336 (Ser); (c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val), wherein the amino acid percent identity is determined using a FASTA program with ktup=1, gap opening penalty=10, gap extension penalty=1, and substitution matrix=BLOSUM62, with other parameters set as default. In one embodiment, the isolated polynucleotide disclosed above is selected from the group consisting of: (a) a polynucleotide sequence as shown in SEQ ID NO:1 from nucleotide 199 to nucleotide 639; (b) a polynucleotide sequence as shown in SEQ ID NO:1 from nucleotide 640 to nucleotide 1206; (c) a polynucleotide sequence as shown in SEQ ID NO:1 from nucleotide 640 to nucleotide 1266; and (d) a polynucleotide sequence as shown in SEQ ID NO:1 from nucleotide 199 to nucleotide 1266. In another embodiment, the isolated polynucleotide disclosed above comprises nucleotide 1 to nucleotide 1068 of SEQ ID NO:3. In another embodiment, the isolated polynucleotide disclosed above encodes a polypeptide that comprises a sequence of amino acid residues selected from the group consisting of: (a) the amino acid sequence as shown in SEQ ID NO:2 from amino acid number 1 (Met), to amino acid number 147 (Ala); (b) the amino acid sequence as shown in SEQ ID NO:2 from amino acid number 148 (Asn), to amino acid number 336 (Ser); (c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val).

In a second aspect, the present invention provides an expression vector comprising the following operably linked elements: a transcription promoter; a DNA segment encoding a zmse1 polypeptide as shown in SEQ ID NO:2 from amino acid number 1 (Met), to amino acid number 356 (Val); and a transcription terminator, wherein the promoter is operably linked to the DNA segment, and the DNA segment is operably linked to the transcription terminator.

In a third aspect, the present invention provides an expression vector as disclosed above, further comprising a secretory signal sequence operably linked to the DNA segment.

In a fourth aspect, the present invention provides a cultured cell comprising an expression vector as disclosed above, wherein the cell expresses a polypeptide encoded by the DNA segment.

In another aspect, the present invention provides a DNA construct encoding a fusion protein, the DNA construct comprising: a first DNA segment encoding a polypeptide comprising a sequence of amino acid residues selected from the group consisting of: (a) the amino acid sequence as shown in SEQ ID NO:2 from amino acid number 1 (Met), to amino acid number 147 (Ala); (b) the amino acid sequence as shown in SEQ ID NO:2 from amino acid number 148 (Asn), to amino acid number 336 (Ser); (c) the amino acid sequence as shown in SEQ ID NO:2 from amino acid number 148 (Asn), to amino acid number 356 (Ser); (d) the amino acid sequence as shown in SEQ ID NO:2 from amino acid number 337 (Arg), to amino acid number 356 (Ser); and (e) the amino acid sequence as shown in SEQ ID NO:2 from amino acid number 1 (Met), to amino acid number 356 (Val); and at least one other DNA segment encoding an additional polypeptide, wherein the first and other DNA segments are connected in-frame; and wherein the first and other DNA segments encode the fusion protein.

In another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

In another aspect, the present invention provides a cultured cell comprising an expression vector as disclosed above, wherein the cell expresses a polypeptide encoded by the DNA construct.

In another aspect, the present invention provides a method of producing a fusion protein comprising: culturing a cell as disclosed above; and isolating the polypeptide produced by the cell.

In another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 1 (Met), to amino acid number 147 (Ala); (b) the amino acid sequence as shown in SEQ ID NO:2 from amino acid number 148 (Asn), to amino acid number 336 (Ser); (c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val), wherein the amino acid percent identity is determined using a FASTA program with ktup=1, gap opening penalty=10, gap extension penalty=1, and substitution matrix=BLOSUM62, with other parameters set as default. In one embodiment, the isolated polypeptide disclosed above comprises a sequence of amino acid residues selected from the group consisting of: (a) the amino acid sequence as shown in SEQ ID NO:2 from amino acid number 1 (Met), to amino acid number 147 (Ala); (b) the amino acid sequence as shown in SEQ ID NO:2 from amino acid number 148 (Asn), to amino acid number 336 (Ser); (c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val).

In another aspect, the present invention provides a method of producing a zmse1 polypeptide comprising: culturing a cell as disclosed above; and isolating the zmse1 polypeptide produced by the cell.

In another aspect, the present invention provides a method of producing an antibody to zmse1 polypeptide comprising: inoculating an animal with a polypeptide selected from the group consisting of: (a) a polypeptide consisting of 13 to 343 amino acids, wherein the polypeptide is identical to a contiguous sequence of amino acids in SEQ ID NO:2 from amino acid number 1 (Met) to amino acid number 356 (Val); (b) a polypeptide as disclosed above; (c) a polypeptide consisting of the amino acid sequence of SEQ ID NO:2 from amino acid number 337 (Arg) to amino acid number 356 (Val); (d) a polypeptide consisting of the amino acid sequence of SEQ ID NO:2 from amino acid number 96 (Glu) to amino acid number 101 (Asp); (e) a polypeptide consisting of the amino acid sequence of SEQ ID NO:2 from amino acid number 226 (Asp) to amino acid number 231 (Asp); (f) a polypeptide consisting of the amino acid sequence of SEQ ID NO:2 from amino acid number 346 (Met) to amino acid number 351 (Glu); (g) a polypeptide consisting of the amino acid sequence of SEQ ID NO:2 from amino acid number 360 (Arg) to amino acid number 365 (Glu); (h) a polypeptide consisting of the amino acid sequence of SEQ ID NO:2 from amino acid number 347 (Asp) to amino acid number 352 (Asp); and (i) a polypeptide consisting of the amino acid sequence of SEQ ID NO:2 from amino acid number 348 (Glu) to amino acid number 353 (Glu); and wherein the polypeptide elicits an immune response in the animal to produce the antibody; and isolating the antibody from the animal.

In another aspect, the present invention provides an antibody produced by the method disclosed above, which binds to a zmse1 polypeptide. In one embodiment, the antibody disclosed above is a monoclonal antibody. In another aspect, the present invention provides an antibody which specifically binds to a polypeptide as disclosed above.

In another aspect, the present invention provides An antibody which specifically binds to a polypeptide disclosed above.

In another aspect, the present invention provides a method of detecting, in a test sample, the presence of a modulator of zmse1 protein activity, comprising: culturing a cell into which has been introduced an expression vector as disclosed above, wherein the cell expresses the zmse1 protein encoded by the DNA segment in the presence and absence of a test sample; and comparing levels of activity of zmse1 in the presence and absence of a test sample, by a biological or biochemical assay; and determining from the comparison, the presence of modulator of zmse1 activity in the test sample.

In another aspect, the present invention provides a method for detecting a genetic abnormality in a patient, comprising: obtaining a genetic sample from a patient; producing a first reaction product by incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence; visualizing the first reaction product; and comparing said first reaction product to a control reaction product from a wild type patient, wherein a difference between said first reaction product and said control reaction product is indicative of a genetic abnormality in the patient.

In another aspect, the present invention provides a method for detecting a cancer in a patient, comprising: obtaining a tissue or biological sample from a patient; incubating the tissue or biological sample with an antibody of claim 19 under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase or decrease in the level of antibody bound to the patient tissue or biological sample relative to the normal control tissue or biological sample is indicative of a cancer in the patient.

In another aspect, the present invention provides a method for detecting a cancer in a patient, comprising: obtaining a tissue or biological sample from a patient; labeling a polynucleotide comprising at least 14 contiguous nucleotides of SEQ ID NO:1 or the complement of SEQ ID NO:1; incubating the tissue or biological sample with under conditions wherein the polynucleotide will hybridize to complementary polynucleotide sequence; visualizing the labeled polynucleotide in the tissue or biological sample; and comparing the level of labeled polynucleotide hybridization in the tissue or biological sample from the patient to a normal control tissue or biological sample, wherein an increase or decrease in the labeled polynucleotide hybridization to the patient tissue or biological sample relative to the normal control tissue or biological sample is indicative of a cancer in the patient.

Within another aspect, the present invention provides a transgenic mouse, wherein the mouse over-expresses residue 1 (Met) to residue 356 (Val) of SEQ ID NO:2) or residue 1 (Met) to residue 349 (Val) of SEQ ID NO:5. In one embodiment, the transgenic mouse disclosed above expresses residue 1 (Met) to residue 356 (Val) of SEQ ID NO:2) or residue 1 (Met) to residue 349 (Val) of SEQ ID NO:5 using a tissue-specific or tissue-restricted promoter. In another embodiment, the transgenic mouse disclosed above expresses residue 1 (Met) to residue 356 (Val) of SEQ ID NO:2) or residue 1 (Met) to residue 349 (Val) of SEQ ID NO:5 using an epithelial-specific, colon-specific, or ovary-specific promoter. In another embodiment, the transgenic mouse disclosed above does not expresses residue 1 (Met) to residue 349 (Val) of SEQ ID NO:5, relative to a normal mouse.

These and other aspects of the invention will become evident upon reference to the following detailed description of the invention and attached drawings.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075, 1985; Nilsson et al., *Methods Enzymol.* 198:3, 1991), glutathione S transferase (Smith and Johnson, Gene 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" (also, "N-Terminal") and "carboxyl-terminal" (also "C-terminal") are used herein to denote positions within polypeptides.

Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGAGCTT-3' are 5'-AGCTTgagt-3' and 3'-tcgacTACC-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure, for example, comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a protein having a CRIB motif (Burbelo, P. D. et al., *J. Biol. Chem.* 270:29071–29074, 1995). The polypeptide has been designated zmse1. The novel zmse1 was found and its corresponding cDNA was sequenced. The novel polypeptide encoded by the cDNA showed limited homology with MSE55 (Bahou, W. F., et al., *J. Biol. Chem.* 267:13986–13992, 1994; Burbelo, P. D. et al., *Proc. Natl. Acad. Sci. USA* 96:9083–9088, 1999). The zmse1 polynucleotide sequence encodes the entire coding sequence of the predicted protein. Zmse1 is a novel protein that may be involved in regulating actin polymerization and resulting structures, cytoskeletal organization, proliferation, cell transformation, motility, cell invasion, metastasis, transport or secretion, tissue contractility, involved in an apoptotic cellular pathway, or the like.

The sequence of the zmse1 polypeptide was deduced from a single clone that contained its corresponding polynucleotide sequence. The clone was obtained from a human K562 cell (ATCC Cat. No. CCL 243) library. Other libraries that might also be searched for such sequences include tumor cell and tissue libraries PBLs, testis, gastrointestinal, prostate, lung, adrenal gland, and the like.

The nucleotide sequence of a representative human zmse1-encoding DNA is described in SEQ ID NO:1, and its deduced 356 residue amino acid sequence is described in SEQ ID NO:2. In its entirety, the human zmse1 polypeptide (SEQ ID NO:2) represents a full-length polypeptide segment (residue 1 (Met) to 356 (Val) of SEQ ID NO:2). The domains and structural features of the zmse1 polypeptide are further described below.

Figure 1C:
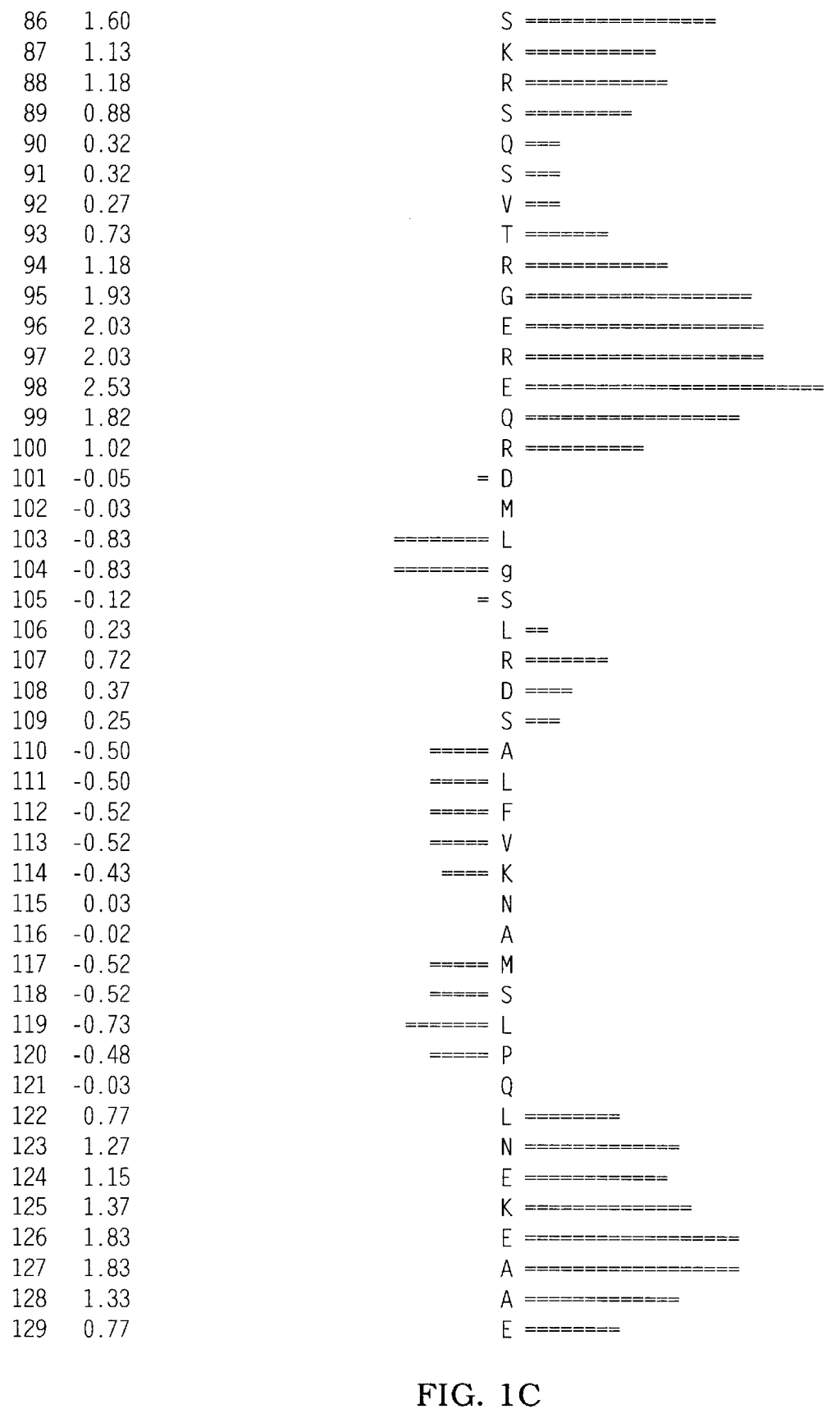
Figure 1E:
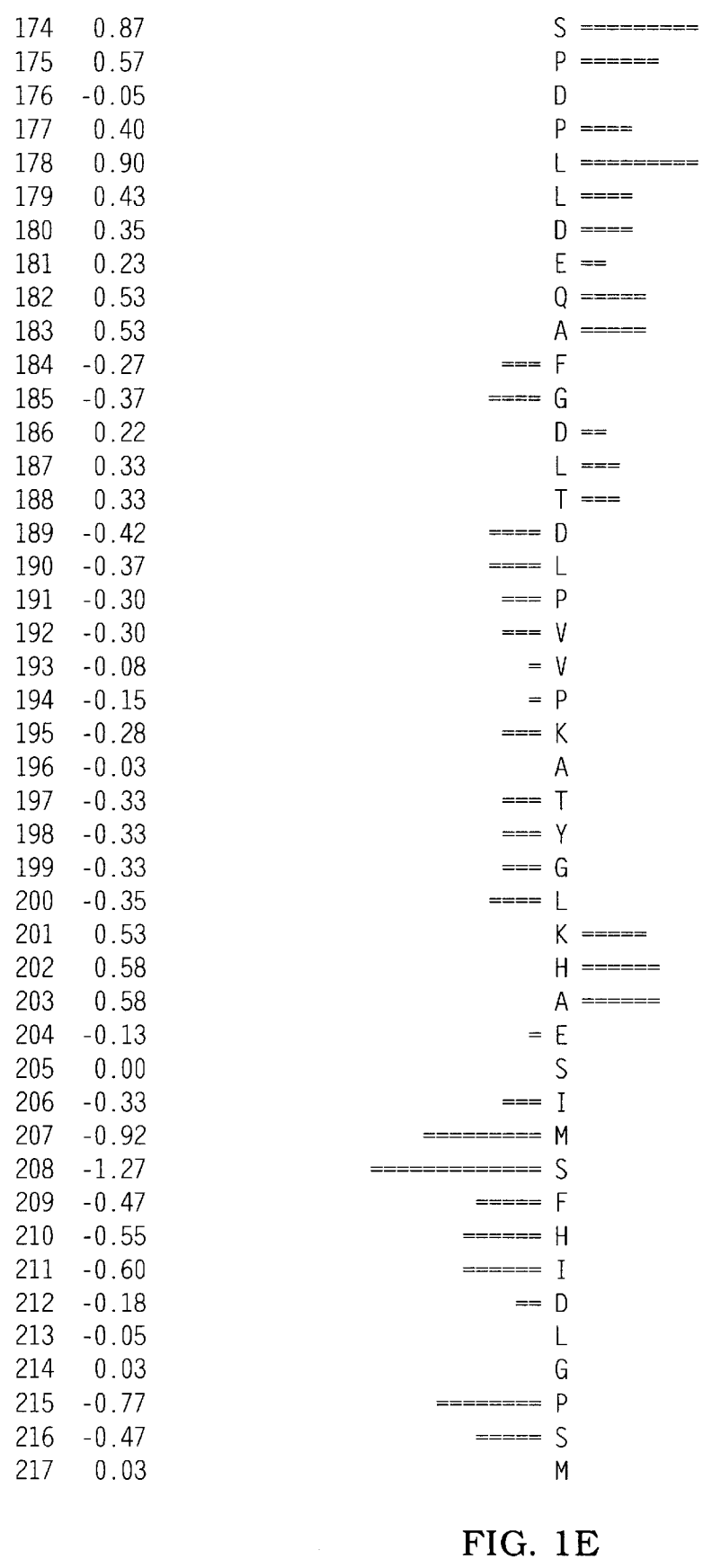
Figure 1F:
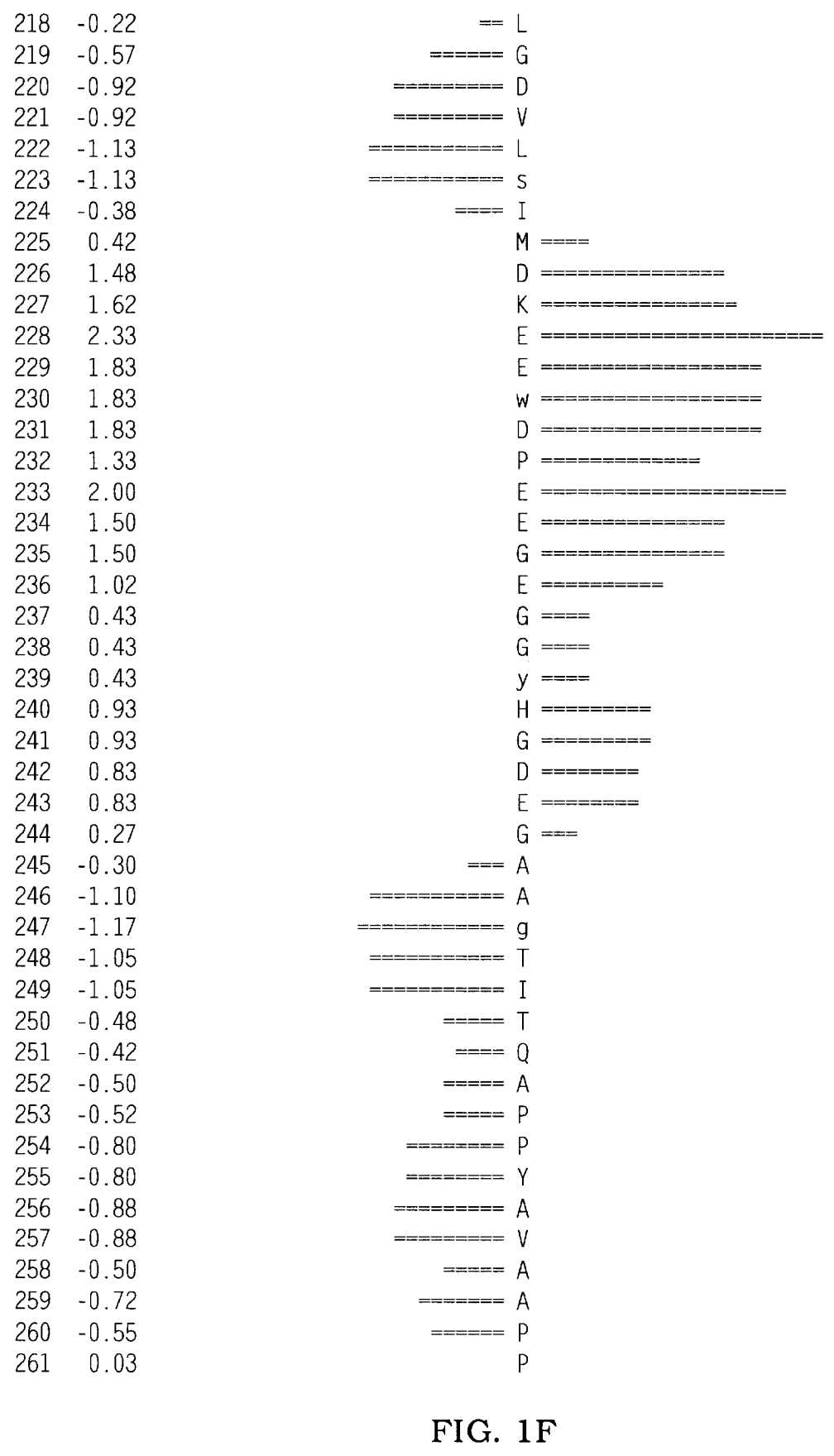
Figure 1I:
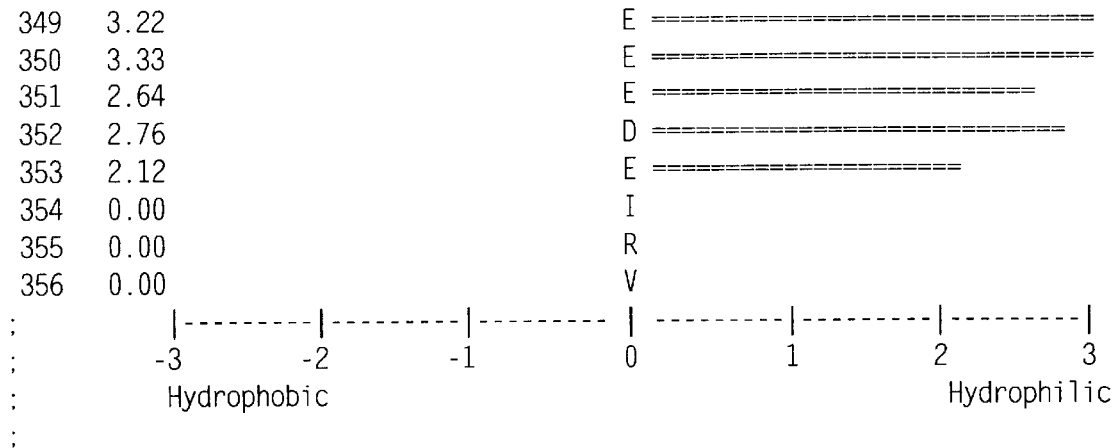

Analysis of the zmse1 polypeptide encoded by the DNA sequence of SEQ ID NO:1 revealed an open reading frame encoding 356 amino acids (SEQ ID NO:2) comprising a mature polypeptide. Zmse1 contains a CRIB motif (SEQ ID NO:6) comprising amino acid residue number 27 (Ile) to amino acid residue number 41 (Gly) of SEQ ID NO:2. This CRIB motif is conserved and identical in both the human and murine forms of zmse1 (see, FIG. 1; and, amino acid residue number 27 (Ile) to amino acid residue number 41 (Gly) of SEQ ID NO:2 and SEQ ID NO:5), suggesting that a minor sequence difference therein could affect the binding of this effector with its target. For example, amino acid mutations in the CRIB motif of MSE55 and a single point mutation in the CRIB motif of WASP decrease or abolish Cdc42 binding and hence the biological activity associated therewith (See, Burbelo, P. D. et al., *Proc. Natl. Acad. Sci. USA* supra.; and Miki, H. et al., *Nature* 391:93–96, 1998). However, sequences outside the CRIB motif are also important for the activity of these effector proteins (See, Zohn, I. M. et al., *Oncogene* 17:1415–1438, 1998). Moreover, zmse1 contains a highly conserved N-terminal domain of approximately 150 amino acid residues (residues 1 (Met) to 147 (Ala) of SEQ ID NO:2; and residues 1 (Met) to 145 (Ala) of SEQ ID NO:5); and a more variable C-terminal domain of approximately 180 amino acid residues compressing residues 148 (Asn) to 336 (Ser) of SEQ ID NO:2, and residues 146 (Asp) to 329 (Pro) of SEQ ID NO:5); and a highly conserved C-terminal tail comprising residues 337 (Arg) to 356 (Val) of SEQ ID NO:2, and 329 (Arg) to 350 (Val) of SEQ ID NO:5. Moreover zmse1 contains several phosphorylation sites that are conserved between the human and mouse polypeptides, and are shown in SEQ ID NO:2 as follows: $Ser_{295}$-$Ala_{296}$-$Arg_{297}$; $Ser_{86}$-$Lys_{87}$-$Arg_{88}$; $Ser_{14}$-$Lys_{15}$-$Arg_{16}$; $Ser_{105}$-$Lue_{106}$-$Arg_{107}$; $Ser_{80}$-$Arg_{81}$-$Lys_{82}$; and $Thr_{303}$-$Thr_{304}$-$Arg_{305}$. The corresponding phosphorylation sites can be determined with reference to FIG. 2 and SEQ ID NO:5. As zmse1 is likely involved in signal transduction, some or all of these phosphorylation sites may be essential for zmse1 activity. Those skilled in the art will recognize that these domain boundaries are approximate, and are based on alignments with known proteins and predictions of protein folding. The corresponding polynucleotides encoding the zmse1 polypeptide regions, domains, motifs, residues and sequences described above are as shown in SEQ ID NO:1 (human zmse1) and SEQ ID NO:4 (mouse zmse1).

The presence of conserved motifs, such as the CRIB motif, and low variance motifs generally correlates with or defines important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they may relate to or define important structures and activities such as guanosine nucleotide binding domains, activation domains, biological and enzymatic activity, signal transduction, cell-cell interaction, tissue or intracellular localization domains and the like. For example, alignment of zmse1 with related polypeptides, for example MSE55, and the presence of a conserved CRIB motif supports that the correlating structural and functional domains of zmse1 are significant in determining that zmse1 is a Rho family effector.

The regions of conserved amino acid residues in zmse1, described above, can be used as tools to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zmse1 sequences are useful for this purpose. Designing and using such degenerate primers may be readily performed by one of skill in the art.

The present invention also provides polynucleotide molecules, including DNA and RNA molecules, that encode the zmse1 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the human zmse1 polypeptide of SEQ ID NO:2. Those skilled in the art will recognize that the degenerate sequence of SEQ ID NO:3 also provides all RNA sequences encoding SEQ ID NO:2 by substituting U for T. Thus, zmse1 polypeptide-encoding polynucleotides comprising nucleotide 1 to nucleotide 1068 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC, TGT | TGY |
| Ser | S | AGC, AGT, TCA, TCC, TCG, TCT | WSN |
| Thr | T | ACA, ACC, ACG, ACT | ACN |
| Pro | P | CCA, CCC, CCG, CCT | CCN |
| Ala | A | GCA, GCC, GCG, GCT | GCN |
| Gly | G | GGA, GGC, GGG, GGT | GGN |
| Asn | N | AAC, AAT | AAY |
| Asp | D | GAC, GAT | GAY |
| Glu | E | GAA, GAG | GAR |
| Gln | Q | CAA, CAG | CAR |
| His | H | CAC, CAT | CAY |
| Arg | R | AGA, AGG, CGA, CGC, CGG, CGT | MGN |
| Lys | K | AAA, AAG | AAR |
| Met | M | ATG | ATG |
| Ile | I | ATA, ATC, ATT | ATH |
| Leu | L | CTA, CTC, CTG, CTT, TTA, TTG | YTN |
| Val | V | GTA, GTC, GTG, GTT | GTN |
| Phe | F | TTC, TTT | TTY |
| Tyr | Y | TAC, TAT | TAY |
| Trp | W | TGG | TGG |
| Ter | . | TAA, TAG, TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., Nuc. Acids Res. 8:1893–912, 1980; Haas, et al. Curr. Biol. 6:315–24, 1996; Wain-Hobson, et al., Gene 13:355–64, 1981; Grosjean and Fiers, Gene 18:199–209, 1982; Holm, Nuc. Acids Res. 14:3075–87, 1986; Ikemura, J. Mol. Biol. 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., Molecular Cloning: A Laboratory Manual, Second Edition (Cold Spring Harbor Press 1989); Ausubel et al., (eds.), Current Protocols in Molecular Biology (John Wiley and Sons, Inc. 1987); Berger and Kimmel (eds.), Guide to Molecular Cloning Techniques, (Academic Press, Inc. 1987); and Wetmur, Crit. Rev. Biochem. Mol. Biol. 26:227, 1990). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20–25° C. below the calculated $T_m$. For smaller probes (e.g., <50 base pairs) hybridization is typically carried out at the $T_m$ or 5–10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40–50% formamide, up to about 6×SSC, about 5×Denhardt's solution, zero up to about 10% dextran sulfate, and about 10–20 µg/ml denatured commercially-available carrier DNA. Generally, such stringent conditions include temperatures of 20–70° C. and a hybridization buffer containing up to 6×SSC and 0–50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the $T_m$, hybridization and wash solutions used, and are routinely determined empirically and experimentally by one of skill in the art.

As previously noted, the isolated polynucleotides of the present invention include DNA and RNA. Methods for preparing DNA and RNA are well known in the art. In general, RNA is isolated from a tissue or cell that produces large amounts of zmse1 RNA. Such tissues and cells are identified by Northern blotting (Thomas, *Proc. Natl. Acad. Sci. USA* 77:5201, 1980), and include intestinal tissues, prostate, ovary, testis, spleen, pancreas, heart, skeletal muscle and the like. Total RNA can be prepared using guanidinium isothiocyanate extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding zmse1 polypeptides are then identified and isolated by, for example, hybridization or PCR.

A full-length clone encoding zmse1 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zmse1, ligand fragments, or other specific binding partners.

Zmse1 polynucleotide sequences disclosed herein can also be used as probes or primers to clone 5' non-coding regions of a zmse1 gene. In view of the tissue-specific expression observed for zmse1 by Northern blotting, this gene region may provide for expression in many cell and tissue types. Promoter elements from a zmse1 gene could thus be used to direct the ubiquitous expression of heterologous genes in, for example, transgenic animals or patients treated with gene therapy. Cloning of 5' flanking sequences also facilitates production of zmse1 proteins by "gene activation" as disclosed in U.S. Pat. No. 5,641,670. Briefly, expression of an endogenous zmse1 gene in a cell is altered by introducing into the zmse1 locus a DNA construct comprising at least a targeting sequence, a regulatory sequence, an exon, and an unpaired splice donor site. The targeting sequence is a zmse1 5' non-coding sequence that permits homologous recombination of the construct with the endogenous zmse1 locus, whereby the sequences within the construct become operably linked with the endogenous zmse1 coding sequence. In this way, an endogenous zmse1 promoter can be replaced or supplemented with other regulatory sequences to provide enhanced, tissue-specific, or otherwise regulated expression.

The polynucleotides of the present invention can also be synthesized using DNA synthesis machines. If chemically synthesized double stranded DNA is required for an application such as the synthesis of a DNA or a DNA fragment, then each complementary strand is made separately, for example via the phosphoramidite method known in the art. The production of short polynucleotides (60 to 80 bp) is technically straightforward and can be accomplished by synthesizing the complementary strands and then annealing them. However, for producing longer polynucleotides (longer than about 300 bp), special strategies are usually employed. For example, synthetic DNAs (double-stranded) are assembled in modular form from single-stranded fragments that are from 20 to 100 nucleotides in length. One method for building a synthetic DNA involves producing a set of overlapping, complementary oligonucleotides. Each internal section of the DNA has complementary 3' and 5' terminal extensions designed to base pair precisely with an adjacent section. After the DNA is assembled, the process is completed by ligating the nicks along the backbones of the two strands. In addition to the protein coding sequence, synthetic DNAs can be designed with terminal sequences that facilitate insertion into a restriction endonuclease site of a cloning vector. Alternative ways to prepare a full-length DNA are also known in the art. See Glick and Pasternak, *Molecular Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are zmse1 polypeptides from other mammalian species, including murine, porcine, ovine, bovine, canine, feline, equine, and other primate polypeptides. Orthologs of human zmse1 can be cloned using information and compositions provided by the present invention in combination with conventional cloning techniques. For example, a cDNA can be cloned using mRNA obtained from a tissue or cell type that expresses zmse1 as disclosed herein. Suitable sources of mRNA can be identified by probing Northern blots with probes designed from the sequences disclosed herein. A library is then prepared from mRNA of a positive tissue or cell line. A zmse1-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zmse1 sequence disclosed herein. Within an additional method, the cDNA library can be used to transform or transfect host cells, and expression of the cDNA of interest can be detected with an antibody to zmse1 polypeptide. Similar techniques can also be applied to the isolation of genomic clones.

A polynucleotide sequence for the mouse ortholog of human zmse1 has been identified and cloned and is shown in SEQ ID NO:4 and the corresponding amino acid sequence shown in SEQ ID NO:5. Analysis of the mouse zmse1 polypeptide encoded by the DNA sequence of SEQ ID NO:4 revealed an open reading frame encoding 349 amino acids (SEQ ID NO:5) comprising a CRIB motif, N-terminal domain, C-terminal domain, and C-terminal tail as described above. A comparison of the human and mouse amino acid sequences reveals that both the human and orthologous polypeptides contain corresponding structural features described above (See, FIG. 2). There is about 78% identity between the mouse and human amino acid sequences over the entire amino acid sequence corresponding to SEQ ID NO:2 and SEQ ID NO:5. There is about 100% identity over the CRIB motif corresponding to amino acid residue 27 (Ile) to amino acid residue 41 (Gly) of SEQ ID NO:2 and SEQ ID NO:5. There is about 91% identity a between the mouse and human zmse1 sequences over the conserved N-terminal domain corresponding to residues 1 (Met) to 147 (Ala) of SEQ ID NO:2; and residues 1 (Met) to 145 (Ala) of SEQ ID NO:5. There is about 73% identity a between the mouse and human zmse1 sequences over the variable C-terminal domain corresponding to residues 148 (Asn) to 336 (Ser) of SEQ ID NO:2, and residues 146 (Asp) to 329 (Pro) of SEQ ID NO:5). There is about 95% identity a between the mouse and human zmse1 sequences over the conserved C-terminal tail corresponding to residues 337 (Arg) to 356 (Val) of SEQ ID NO:2, and 330 (Arg) to 349 (Val) of SEQ ID NO:5. The above percent identities were determined using a FASTA program with ktup=1, gap opening penalty=12, gap extension penalty=2, and substitution matrix=BLOSUM62, with other parameters set as default. The corresponding polynucleotides encoding the mouse zmse1 polypeptide regions, domains, motifs, residues and sequences described above are as shown in SEQ ID NO:4.

Those skilled in the art will recognize that the sequence disclosed in SEQ ID NO:1 represents a single allele of human zmse1 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zmse1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zmse1 polypeptides that are substantially similar to the polypeptides of SEQ ID NO:2 and their orthologs. The term "substantially similar" is used herein to denote polypeptides having 70%, preferably 80%, more preferably at least 85%, sequence identity to the sequences shown in SEQ ID NO:2 or their orthologs. Such polypeptides will more preferably be at least 90% identical, and most preferably 95% or more identical to SEQ ID NO:2 or its orthologs.) Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zmse1. The FASTA algorithm is described by Pearson and Lipman, *Proc. Nat'l Acad. Sci. USA* 85:2444, 1988; and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.*, supra.

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zmse1 polypeptides or substantially similar zmse1 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from about 330 to about 385 amino acid residues that comprise a sequence that is at least 90%, preferably at least 95%, and more preferably 99% or more identical to the corresponding region of SEQ ID NO:2. Polypeptides comprising affinity tags can further comprise a proteolytic cleavage site between the zmse1 polypeptide and the affinity tag. Preferred such sites include thrombin cleavage sites and factor Xa cleavage sites.

TABLE 4

| Conservative amino acid substitutions | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

The present invention further provides a variety of other polypeptide fusions and related multimeric proteins comprising one or more polypeptide fusions. For example, a zmse1 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zmse1 polypeptide fusions can be expressed in genetically engineered cells to produce a variety of multimeric zmse1 analogs. Auxiliary domains can be fused to zmse1 polypeptides to target them to specific cells, tissues, or macromolecules (e.g., collagen). For example, a zmse1 polypeptide or protein could be targeted to a predetermined cell type by fusing a zmse1 polypeptide to a ligand that specifically binds to a receptor on the surface of the target cell. In this way, polypeptides and proteins can be targeted for therapeutic or diagnostic purposes. A zmse1 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993). A limited number of non-conservative amino acids, amino acids that are not encoded by the genetic code, non-naturally occurring amino acids, and unnatural amino acids may be substituted for zmse1 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor or other biochemical interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related phosphodiesterases.

Determining amino acid residues that are within regions or domains that are critical to maintaining structural integrity is within the skill of one in the art. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372–376, 1995 and Cordes et al., *Current Opin. Struct. Biol.* 6:3–10, 1996). In general, when designing modifications to molecules or identifying specific fragments determination of structure will be accompanied by evaluating activity of modified molecules.

Amino acid sequence changes are made in zmse1 polypeptides so as to minimize disruption of higher order structure essential to biological activity. For example, when the zmse1 polypeptide comprises one or more helices, changes in amino acid residues will be made so as not to disrupt the helix geometry and other components of the molecule where changes in conformation abate some critical function, for example, binding of the molecule to its binding partners, or enzymatic function. The effects of amino acid sequence changes can be predicted by, for example, computer modeling as disclosed above or determined by analysis of crystal structure (see, e.g., Lapthorn et al., *Nat. Struct. Biol.* 2:266–268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205–214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961–964, 1992).

A Hopp/Woods hydrophilicity profile of the zmse1 protein sequence as shown in SEQ ID NO:2 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored (See, Figure 1). For example, in zmse1, hydrophilic regions include: (1) amino acid number 96 (Glu) to amino acid number 101 (Asp) of SEQ ID NO:2; (2) amino acid number 226 (Asp) to amino acid number 231 (Asp) of SEQ ID NO:2; (3) amino acid number 346 (Met) to amino acid number 351 (Glu) of SEQ ID NO:2; (4) amino acid number 347 (Asp) to amino acid number 352 (Asp) of SEQ ID NO:2; and (5) amino acid number 348 (Glu) to amino acid number 353 (Glu) of SEQ ID NO:2.

Those skilled in the art will recognize that hydrophilicity or hydrophobicity is taken into account when designing modifications in the amino acid sequence of a zmse1 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp; for example, residues tolerant of substitution could include such residues as shown in SEQ ID NO:2. Cysteine residues will be relatively intolerant of substitution.

The identities of essential amino acids can also be inferred from analysis of sequence similarity between known phosphodiesterase family members with zmse1. Using methods such as "FASTA" analysis described previously, regions of high similarity are identified within a family of proteins and used to analyze amino acid sequence for conserved regions. An alternative approach to identifying a variant zmse1 polynucleotide on the basis of structure is to determine whether a nucleic acid molecule encoding a potential variant zmse1 polynucleotide can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081, 1989; Bass et al., *Proc. Natl Acad. Sci. USA* 88:4498, 1991; Coombs and Corey, "Site-Directed Mutagenesis and Protein Engineering," in *Proteins: Analysis and Design*, Angeletti (ed.), Academic Press, Inc., pp. 259–311, 1998). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699, 1996.

The present invention also includes functional fragments of zmse1 polypeptides and nucleic acid molecules encoding such functional fragments. A "functional" zmse1 or fragment thereof defined herein is characterized by its proliferative or differentiating activity, by its ability to induce or inhibit specialized cell functions, or by its ability to bind specifically to an anti-zmse1 antibody or zmse1 substrate or binding partner (either soluble or immobilized).

Routine deletion analyses of nucleic acid molecules can be performed to obtain functional fragments of a nucleic acid molecule that encodes a zmse1 polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for zmse1 activity, or for the ability to bind anti-zmse1 antibodies or zmse1 substrate or binding partner. One alternative to exonuclease digestion is to use oligonucleotide-directed mutagenesis to introduce deletions or stop codons to specify production of a desired zmse1 fragment. Alternatively, particular fragments of a zmse1 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507, 1995. Moreover, standard techniques for functional analysis of proteins are described by, for example, Treuter et al., *Molec. Gen. Genet.* 240: 113, 1993; Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), Nijhoff, pp. 65–72, 1987; Herschman, "The EGF Receptor," in *Control of Animal Cell Proliferation* 1, Boynton et al. (eds.), Academic Press, pp. 169–199, 1985; Coumailleau et al., *J. Biol. Chem.* 270:29270, 1995; Fukunaga et al., *J. Biol. Chem.* 270:25291, 1995; Yamaguchi et al., *Biochem. Pharmacol.* 50: 1295, 1995; and Meisel et al., *Plant Molec. Biol.* 30:1, 1996.

In addition, the proteins of the present invention (or polypeptide fragments thereof) can be joined to other bioactive molecules, particularly other CRIB proteins or Rho effectors, to provide multi-functional molecules. For example, one or more domains or sub-fragments from zmse1 can be joined to other CRIB proteins to enhance their biological properties or efficiency of production.

The present invention thus provides a series of novel, hybrid molecules in which a segment comprising one or more of the domains or motifs of zmse1 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zmse1 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., those with CRIB protein activity, that induce signal transduction, that exhibit Cdc42/Rac or other Rho protein binding, that bind anti-zmse1 antibodies, and the like) can be recovered from the host cells and rapidly sequenced. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or that retain, for example, CRIB protein-like properties, protein binding activity, cytoskeletal rearranging activity, proliferation, induction of actin polymerization, cell motility or invasion, cell-cell communication, or signal transduction activity of the wild-type zmse1 protein. For example, using the methods described herein, one could identify a substrate binding domain in addition to the CRIB domain on zmse1; heterodimeric and homodimeric binding domains; guanosine nucleotide binding domains; other enzymatically active domains; other functional or structural domains; or other domains important for protein-protein interactions, biological activity, or signal transduction. Such polypeptides may also include additional polypeptide segments, such as affinity tags, as generally disclosed herein.

For any zmse1 polypeptide, including variants and fusion proteins, one of ordinary skill in the art can readily generate a fully degenerate polynucleotide sequence encoding that variant using the information set forth in Tables 1 and 2 above.

The zmse1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A Laboratory Manual, 2nd ed., Cold Spring Harbor Laboratory Press, Cold Spring Harbor, N.Y., 1989, and Ausubel et al., eds., Current Protocols in Molecular Biology, John Wiley and Sons, Inc., NY, 1987.

In general, a DNA sequence encoding a zmse1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zmse 1 polypeptide into the secretory pathway of a host cell, a secretory signal sequence (also known as a leader sequence, prepro sequence or pre sequence) is provided in the expression vector. The secretory signal sequence may be derived from any secreted protein (e.g., t-PA) or synthesized de novo. The secretory signal sequence is operably linked to the zmse1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841–5, 1982), DEAE-dextran mediated transfection (Ausubel et al., ibid.), and liposome-mediated transfection (Hawley-Nelson et al., Focus 15:73, 1993; Ciccarone et al., Focus 15:80, 1993, and viral vectors (Miller and Rosman, BioTechniques 7:980–90, 1989; Wang and Finer, Nature Med. 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977), NIH 3T3 fibroblasts (ATCC No. CRL-1658), Rat2 cells (ATCC No. CRL-1764), and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of Agrobacterium rhizogenes as a vector for expressing genes in plant cells has been reviewed by Sinkar et al., J. Biosci. (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from Autographa californica nuclear polyhedrosis virus (AcNPV). See, King, L. A. and Possee, R. D., The Baculovirus Expression System: A Laboratory Guide, London, Chapman & Hall; O'Reilly, D. R. et al., Baculovirus Expression Vectors: A Laboratory Manual, New York, Oxford University Press., 1994; and, Richardson, C. D., Ed., Baculovirus Expression Protocols. Methods in Molecular Biology, Totowa, N.J., Humana Press, 1995. The second method of making recombinant baculovirus utilizes a transposon-based system described by Luckow (Luckow, V. A, et al., J Virol 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zmse1 polypeptide into a baculovirus genome maintained in E. coli as a large plasmid called a "bacmid." The pFastBac1™ transfer vector utilizes the AcNPV polyhedrin promoter to drive the expression of the gene of interest, in this case zmse1. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used. Moreover, transfer vectors can be constructed which replace the native zmse1 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zmse1 secretory signal sequence. In addition, transfer vectors can include an in-frame fusion with DNA encoding an epitope tag at the C- or N-terminus of the expressed zmse1 polypeptide, for example, a Glu-Glu epitope tag (Grussenmeyer, T. et al., *Proc. Natl. Acad. Sci.* 82:7952–4, 1985). Using a technique known in the art, a transfer vector containing zmse1 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zmse1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405 ™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the zmse1 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillernondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zmse1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin. Expressed recombinant zmse1 polypeptides (or chimeric zmse1 polypeptides) can be purified using fractionation and/or conventional purification methods and media. For example, the zmse1 polypeptides of the present invention can be purified using glutathione affinity chromatography followed by isopropyl-1-thio-β-D-galactopyranoside, such as that applied to other CRIB proteins (Burbelo, P. D. et al., *J. Biol. Chem.* 270:29071–29074, 1995). Moreover, other conventional purification methods can be used. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides, or anti-complementary polypeptides, to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural or biochemical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529–39). Within additional embodiments of the invention, a fusion of the polypeptide of interest and an affinity tag (e.g., maltose-binding protein, an immunoglobulin domain) may be constructed to facilitate purification. Moreover purification methods used to purify mammalian, or other eukaryotic CRIB polypeptides can be used to purify human zmse1 polypeptides. See, for example, Burbelo, P. D. et al., supra.

Moreover, using methods described in the art, polypeptide fusions, or hybrid zmse1 proteins, are constructed using regions or domains of the inventive zmse1 in combination with those of other Rho effector family proteins (e.g. MSE55, PAK, WASP, other CRIB proteins, and the like), or heterologous proteins (Sambrook et al., ibid.; Altschul et al., ibid.; Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, alter activity in cytoskeletal reorganization or gene transcription in a cell, alter cytoskeletal organization and cell motility, transformation, or invasiveness, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding various components of the fusion protein in the proper reading frame can be generated using known techniques and expressed by the methods described herein. For example, part or all of a domain(s) conferring a structural or biological function may be swapped between zmse1 of the present invention with the functionally equivalent domain(s) from another family member. Such domains include, but are not limited to, the CRIB motif, the N-terminal domain, C-terminal domain, or C-terminal tail. Such fusion proteins would be expected to have a biological functional profile that is the same or similar to polypeptides of the present invention or other known Rho effector family proteins (e.g. binding Cdc42, GTP hydrolysis or binding, increasing or decreasing actin polymerization, cell motility, or transformation, and the like) depending on the fusion constructed. Moreover, such fusion proteins may exhibit other properties as disclosed herein.

Standard molecular biological and cloning techniques can be used to swap the equivalent domains between the zmse1 polypeptide and those polypeptides to which they are fused. Generally, a DNA segment that encodes a domain of interest, e.g., a zmse1 active polypeptide or motif described herein, is operably linked in frame to at least one other DNA segment encoding an additional polypeptide and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a full length or mature polypeptide; or a DNA construct would encode from N-terminus to C-terminus a fusion protein comprising an N-terminal domain containing a CRIB motif and a C-terminal domain; or a DNA construct would encode from N-terminus to C-terminus a fusion protein comprising an N-terminal domain containing a CRIB motif; or, for example, any of the above as interchanged with equivalent regions from another protein. Such fusion proteins can be expressed, isolated, and assayed for activity as described herein.

Zmse1 polypeptides or fragments thereof may also be prepared through chemical synthesis. Zmse1 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is with a reagent which cleaves the polypeptide from the resin and removes most of the side-chain protecting groups. Such methods are well established in the art.

The activity of molecules of the present invention can be measured using a variety of assays that measure actin polymerization, GTP binding or hydrolysis, proliferation, cell motility and invasion, metastasis or other CRIB/Rho effector protein activity. Of particular interest are assays that measure changes in cell proliferation, transformation, adhesion, gene expression, apoptosis, generation of nucleotide monophosphates, cell motility and invasion, metastasis, actin stress fiber production, filopodia, lamellipodia, membrane ruffling and others. Moreover CRIB/Rho effector protein activity can be measured using protein or antibody binding assays, scintillation proximity assay (SPA) technology described herein; cAMP assays described herein; as well as other assays described herein. Such assays are well known in the art, and many are described in further detail below.

As a CRIB protein zmse1 can affect cytoskeletal reorganization, cell-cell interaction and motility and hence can affect tissues that contract. Moreover, zmse1 is expressed in contractile tissues. For example contractile tissues in which zmse1 is expressed include testis, prostate, heart and skeletal muscle. The effects of zmse1 polypeptide, its antagonists and agonists, on tissue contractility can be measured in vitro using a tensiometer with or without electrical field stimulation. Such assays are known in the art and can be applied to tissue samples, such as aortic rings, muscle tissue, and other contractile tissue samples, as well as to organ systems, such as atria, and can be used to determine whether zmse1 polypeptide, its agonists or antagonists, enhance or depress contractility. Molecules of the present invention are hence useful for treating dysfunction associated with contractile tissues or can be used to suppress or enhance contractility in vivo. As such, molecules of the present invention have utility in treating cardiovascular disease, muscle relaxants or stimulants, infertility, in vitro fertilization, birth control, treating impotence or other male reproductive dysfunction, as well as inducing birth.

The effect of the zmse1 polypeptides, antagonists and agonists of the present invention on contractility of tissues including skeletal and smooth muscle tissues, testis, heart, and the like, can be measured in a tensiometer that measures contractility and relaxation in tissues. See, Dainty et al., *J. Pharmacol.* 100:767, 1990; Rhee et al., *Neurotox.* 16: 179, 1995; Anderson, M. B., *Endocrinol.* 114:364–368, 1984; and Downing, S. J. and Sherwood, O. D, *Endocrinol.* 116:1206–1214, 1985. For example, measuring vasodilatation of aortic rings is well known in the art. Briefly, aortic rings are taken from 4 month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to 1 gram resting tension and allowed to stabilize for about one hour before testing. The integrity of the rings can be tested with norepinepherin (Sigma Co., St. Louis, Mo.) and Carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A zmse1 polypeptide, antagonist or agonist sample is then added to 1, 2 or 3 of the 4 baths, without flushing, and tension on the rings recorded and compared to the control rings containing buffer only. Enhancement or relaxation of contractility by zmse1 polypeptides, their agonists and antagonists is directly measured by this method, and it can be applied to other contractile tissues such as skeletal and smooth muscle tissue, gastrointestinal tissues, uterus, prostate, and testis.

The activity of molecules of the present invention can be measured using a variety of assays that measure stimulation of gastrointestinal cell contractility, modulation of nutrient uptake and/or secretion of digestive enzymes. Of particular interest are changes in contractility of smooth muscle cells, for example, the contractile response of segments of mammalian duodenum or other gastrointestinal smooth muscles tissue (Depoortere et al., *J. Gastrointestinal Motility* 1:150–159, 1989, incorporated herein by reference). An exemplary in vivo assay uses an ultrasonic micrometer to measure the dimensional changes radially between commissures and longitudinally to the plane of the valve base (Hansen et al., *Society of Thoracic Surgeons* 60:S384–390, 1995).

Gastric motility is generally measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. A test food or liquid is radiolabeled with an isotope (e.g. $^{99m}$Tc), and after ingestion or administration, transit time through the gastrointestinal tract and gastric emptying are measured by visualization using gamma cameras (Meyer et al., *Am. J. Dig. Dis.* 21:296, 1976; Collins et al., *Gut* 24:1117, 1983; Maughan et al., *Diabet. Med.* 13 9 Supp. 5:S6–10, 1996 and Horowitz et al., *Arch. Intern. Med.* 145:1467–1472, 1985). These studies may be performed before and after the administration of a promotility agent to quantify the efficacy of the drug.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Gamier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Moreover, the activity and effect of zmse1 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315–328,1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zmse1, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zmse1, on the ability of the tumor to recruit vasculature and undergo metastasis can thus be assessed. In addition, aside from using adenovirus, the implanted cells can be transiently transfected with zmse1. Use of stable zmse1 transfectants as well as use of induceable promoters to activate zmse1 expression in vivo are known in the art and can be used in this system to assess zmse1 induction of metastasis. For general reference see, O'Reilly M S, et al. *Cell* 79:315–328, 1994; and Rusciano D, et al. Murine Models of Liver Metastasis. *Invasion Metastasis* 14:349–361, 1995.

The activation of zmse1 polypeptide can be measured by a silicon-based biosensor microphysiometer which measures the extracellular acidification rate or proton excretion associated with zmse1 activation and subsequent physiologic cellular responses. An exemplary device is the Cytosensor™ Microphysiometer manufactured by Molecular Devices, Sunnyvale, Calif. A variety of cellular responses, such as cell proliferation, signal transduction, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. Et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including agonists, ligands, or antagonists of the zmse1 polypeptide. Preferably, the microphysiometer is used to measure responses of a zmse1-expressing eukaryotic cell, compared to a control eukaryotic cell that does not express zmse1 polypeptide. Zmse1-expressing eukaryotic cells comprise cells into which zmse1 has been transfected, as described herein, creating a cell that is responsive to zmse1-modulating stimuli; or cells naturally expressing zmse1. Differences, measured by a change in extracellular acidification, for example, an increase or diminution in the response of cells expressing zmse1, relative to a control, are a direct measurement of zmse1-modulated cellular responses. Moreover, such zmse1-modulated responses can be assayed under a variety of stimuli. Also, using the microphysiometer, there is provided a method of identifying agonists and antagonists of zmse1 polypeptide, comprising providing cells expressing a zmse1 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Antagonists and agonists, including the natural effectors or binding partners of zmse1 polypeptide, can be rapidly identified using this method.

In view of the protein family of which zmse1 is a member, agonists (including the natural ligand/substrate/cofactor/ etc.) and antagonists have enormous potential in both in vitro and in vivo applications. Compounds identified as zmse1 agonists and antagonists are useful for modulating tumor cell motility, invasion, and metastasis, modulating actin polymerization and cytoskeletal reorganization, gene transcription, modulating contractility of various tissues as described herein, modulating proliferation (e.g., of cancerous cells), modulating digestion, modulating heart conditions, modulating testicular function and fertility, and the like in vitro and in vivo. For example, zmse1 and agonist or antagonist compounds are useful as components of defined cell culture media, and may be used alone or in combination with other cytokines and hormones to replace serum that is commonly used in cell culture. Agonists or antagonists are thus useful in specifically promoting the growth and/or development of cell lineages in culture. Alternatively, zmse1 polypeptides and zmse1 agonist or antagonist polypeptides are useful as a research reagent, such as for the expansion of cell lines, or useful as an amino acid source for cell culture.

The activity of molecules of the present invention can be measured using a variety of assays that measure proliferation and/or differentiation of specific cell types, chemotaxis, adhesion, changes in ion channel influx, pH flux, regulation of second messenger levels and neurotransmitter release, cell motility, protein binding, apoptosis, or the like. Such assays are well known in the art. See, for example, in "Basic & Clinical Endocrinology Ser., Vol. 3," *Cytochemical Bioassays: Techniques & Applications*, Chayen; Chayen, Bitensky, eds., Dekker, New York, 1983.

The activity of molecules of the present invention can also be measured using a variety of assays that measure, for example, signal transduction upon binding a ligand or substrate, or antibody binding to the outside of an intact cell and stimulating the signal transduction pathway of zmse1. For example, zmse1 polypeptides, complementary binding polypeptides, or anti-zmse1 antibodies can be labeled and tested for specific and saturating binding to specific substrates, cell lines or cells. Identification of positive cells to which zmse1 polypeptides, complementary binding polypeptides, or anti-zmse1 antibodies binds can be achieved by injecting a radioactively or fluorescently-labeled zmse1 polypeptide, polypeptide fragments, complementary binding polypeptides, or anti-zmse1 antibodies and using art-recognized immunohistochemistry methods to visualize a cell or tissue in vivo where zmse1 binds or is expressed. After identification of bound positive cells, activity can be tested for zmse1-mediated activation of a signal transduction pathway using methods known in the art. For instance, vector constructs containing a reporter (e.g. SRE-luciferase, STAT-luciferase, thyroid hormone response element (THRE)-luciferase, SV40 promoter-luciferase or the like) can be introduced into the positive cell lines expressing zmse1; such cell lines, when exposed to conditioned media containing secreted zmse1 activating proteins will demonstrate zmse1-mediated signal transduction activity through activation of the measurable reporter. Such assays are well known in the art. Specific assays include, but are not limited to, bioassays measuring signal transduction.

The activity of molecules of the present invention can also be measured using a variety of assays that measure, for example, cell motility, adhesion and invasion in vitro and metastasis in vivo. Such assays are known in the art. For example, motility assays in NIH 3T3 cells, mouse keratinocytes, and epithelial cells are described in Takiashi, K. et al., *Mol. Cell Biol.* 13:72–79, 1993; Takiashi, K. et al., *Oncogene* 5:273–278, 1994; Ridley, A. J. et al., *Mol. Cell Biol.* 15:1110–1122, 1995; and Keely, P. J. et al., *Nature* 360:632–636, 1997. For review and application of in vitro invasion assays; for example, using hepatoma or lymphoma cells invasion through mesothelial or fibroblast cell monolayers, phagokenesis and wound healing assays. For example, see Yoshioka, K. et al., *FEBS Lett.* 372:25–28, 1995; Wang, W. Z., and Ron D.*Science* 272:1347–1349, 1996; Habets, G. *Cell* 77:537–549, 1994; and Michiels, F. et al., *Nature* 375:338–340, 1995; Michiels, F. and Collard, J. G., *Biochem. Soc. Symp.* 65:215–146, 1999; and Keely, P. J. supra. Moreover, in vivo metastasis assays can be used to assess zmse1 polypeptide, expression, agonist or antagonist activity in vivo in mice (Verschueren, H. *Eur. J. Cell Biol.*

73:182–187, 1997). Cell adhesion can be assessed by the adherence or non-adherence of normally adherent cell lines to cell culture dishes, amongst other assays known in the art.

Moreover, the activity of molecules of the present invention can also be measured using a variety of assays that measure cytoskeletal reorganization. Such assays are well known in the art. For example, effects of zmse1 on membrane ruffling can be assessed in Swiss 3T3 cells (Ridley, A. J. *Cell* 70:401–410, 1992). Actin polymerization and cytoskeletal rearrangement including assessment of actin stress fibers, focal complexes, lamellipodia and filopodia, can be assessed by various means including immunofluorescence, and time-lapse imaging amongst other known methods (Symons, M. et al., *Cell* 84:723–734, 1996; Nobes, C. D., and Hall, A., *Cell* 81:53–62, 1995; Burbelo, P. D. et al., *Proc. Natl. Acad. Sci. USA* 96:9083–9088, 1999; Aspenstrom, P. *Exper. Cell. Res.* 246:20–25, 1999; Gallo, G., and Letourneau, P. C., *Current Biol.* 8:R80–R82, 1998; and Miki, H. et al., *Nature* 391:93–96, 1998).

Moreover, the activity of molecules of the present invention can also be measured using a variety of assays that measure protein binding. For example, the zmse1 polypeptides of the present invention can be assessed for their ability to bind Rho family proteins, such as Cdc42, Rac and Rho, in filter binding assays with GST-rhoGAP as a positive control (Burbelo, P. D. et al., *J. Biol. Chem.* 270:29071–29074, 1995; and Lancaster, C. A. et al., *J. Biol. Chem.* 269:1137–1142, 1994. Moreover, guanine nucleotide dependence of such binding can also be determined using a glutathione-agarose bead assay or other method known in the art (for example, see Burbelo, P. D. et al., supra.; and Burbelo, P. D. et al., *Proc. Natl. Acad. Sci. USA* 96:9083–9088, 1999). Moreover, GTP hydrolysis can be measured as a product of zmase1 activity. Such assays are known in the art.

Zmse1 can also be used to identify modulators (e.g, agonists or antagonists) of its activity. Test compounds are added to the assays disclosed herein to identify compounds that inhibit or stimulate the activity of zmse1. In addition to those assays disclosed herein, samples can be tested for inhibition/stimulation of zmse1 activity within a variety of assays designed to measure zmse1 binding, dimerization, heterodimerization, DNA binding or the stimulation/inhibition of zmse1-dependent cellular responses. For example, zmse1-expressing cell lines can be transfected with a reporter gene construct that is responsive to a zmse1-stimulated cellular pathway. Reporter gene constructs of this type are known in the art, and will generally comprise a zmse1-DNA response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263:9063–6; 1988 and Habener, *Molec. Endocrinol.* 4:1087–94; 1990. Hormone response elements are reviewed in Beato, *Cell* 56:335–44; 1989. Candidate compounds, solutions, mixtures or extracts or conditioned media from various cell types are tested for the ability to enhance the activity of zmse1 signal transduction as evidenced by an increase in zmse1 stimulation of reporter gene expression. Assays of this type will detect compounds that directly stimulate zmse1 signal transduction activity through binding the upstream receptor or by otherwise stimulating part of the signal cascade in which zmse1 is involved. As such, there is provided a method of identifying agonists of zmse1 polypeptide, comprising providing cells expressing zmse1 responsive to a zmse1 pathway, culturing a first portion of the cells in the absence of a test compound, culturing a second portion of the cells in the presence of a test compound, and detecting a increase in a cellular response of the second portion of the cells as compared to the first portion of the cells. Moreover a third cell, containing the reporter gene construct described above, but not expressing zmse1 polypeptide, can be used as a control cell to assess non-specific, or non-zmse1-mediated, stimulation of the reporter. Agonists are useful to stimulate or increase zmse1 polypeptide function. Moreover, compounds or other samples can be tested for direct blocking of zmse1 binding to another protein or substrate, e.g., a heterodimer described below, using zmse1 tagged with a detectable label (e.g., $^{125}$I, biotin, horseradish peroxidase, FITC, and the like). Within assays of this type, the ability of a test sample to inhibit the binding of labeled zmse1 to the other protein or substrate is indicative of inhibitory activity, which can be confirmed through secondary assays. Proteins used within binding assays may be cellular proteins or isolated, immobilized proteins.

Zmse1 activation can be detected by: (1) measurement of adenylate cyclase activity (Salomon et al., *Anal. Biochem.* 58:541–48, 1974; Alvarez and Daniels, *Anal. Biochem.* 187:98–103, 1990); (2) measurement of change in intracellular cAMP levels using conventional radioimmunoassay methods (Steiner et al., *J. Biol. Chem.* 247:1106–13, 1972; Harper and Brooker, *J. Cyc. Nucl. Res.* 1:207–18, 1975); or (3) through use of a cAMP scintillation proximity assay (SPA) method (Amersham Corp., Arlington Heights, Ill.). These methods provide sensitivity and accuracy.

An alternative assay system involves selection of polypeptides that are able to induce expression of a cyclic AMP response element (CRE)-luciferase reporter gene, as a consequence of elevated cAMP levels, in cells expressing a zmse1 polypeptide, but not in cells lacking zmse1 expression, analogous to such assays employing calcitonin receptor as described in U.S. Pat. No. 5,622,839, U.S. Pat. No. 5,674,689, and U.S. Pat. No. 5,674,981.

In addition, polypeptides of the present invention can be assayed and used for their ability to modify inflammation. As zmse1 may induce cell migration and/or affect contractility in tissues, it may be involved in migration of inflammatory cells. Methods to determine proinflammatory and anti-inflammatory qualities of zmse1 polypeptide, its agonists or antagonists, are known in the art and discussed herein. For example, suppression of cAMP production is an indication of anti-inflammatory effects (Nihei, Y., et al., *Arch. Dermatol. Res.*, 287:546–552, 1995). Suppression of cAMP and inhibition of ICAM and HLA-Dr induced by IFN-γ in keratinocytes can be used to assess inhibition of inflammation. Alternatively, enhancement of cAMP production and induction of ICAM and HLA-Dr in this system can be an measurement of proinflammatory effects of a protein. As a member of a signal transduction cascade, zmse1, likewise can exhibit similar inflammatory effects, and may exert these effects in tissues in which it is expressed, or indirectly in other tissues. For example, zmse1 is expressed in the heart and skeletal muscle, and can be useful in promoting wound healing in this tissue, or exhibit anti-bacterial or anti-viral effects. Moreover, zmse1, its agonists or antagonists can be useful in treatment of inflammatory heart or cardiovascular conditions, muscle inflammation, inflammation during and after surgery, arthritis, asthma, inflammatory bowel disease, diverticulitis, and the like.

Moreover, direct measurement of zmse1 polypeptide and anti-zmse1 antibodies can be useful in diagnosing inflammatory diseases such as reperfusion ischemia, inflammatory bowel disease, diverticulitis, asthma, pelvic inflammatory disease (PID), psoriasis, arthritis, melanoma, and other inflammatory diseases. Moreover zmse1 antagonists can be useful in treatment of myocarditis, atherosclerosis, pelvic inflammatory disease, (PID), psoriasis, arthritis, eczema, scieroderma, and other inflammatory diseases.

As such, zmse1 polypeptide, agonists or its antagonists, have potential uses in inflammatory diseases such as asthma and arthritis. For example, if zmse1 is proinflammatory, antagonists would be valuable in asthma therapy or other anti-inflammatory therapies where migration of lymphocytes is damaging. In addition, zmse1 can serve other important roles in lung function, for instance, bronchodilation, tissue elasticity, recruitment of lymphocytes in lung infection and damage. Assays to assess the activity of zmse1 in lung cells are discussed in Laberge, S. et al., *Am. J. Respir. Cell Mol. Biol.* 17:193–202, 1997; Rumsaeng, V. et al., *J. Immunol.*, 159:2904–2910, 1997; and Schluesener, H. J. et al., *J. Neurosci. Res.* 44:606–611, 1996. Methods to determine proinflammatory and antiinflammatory qualities of zmse1 its agonists or its antagonists are known in the art. Moreover, other molecular biological, immunological, and biochemical techniques known in the art and disclosed herein can be used to determine zmse1 activity and to isolate agonists and antagonists.

The activity of molecules of the present invention may be measured using a variety of assays that, for example, measure neogenesis or hyperplasia (i.e., proliferation) of cardiac or other cells based on the potential effects of activity of zmse1 in those tissues. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured in vitro using cultured cells or in vivo by administering molecules of the present invention to the appropriate animal model. Generally, proliferative effects are seen as an increase in cell number, and may include inhibition of apoptosis as well as stimulation of mitogenesis. Cultured cells for use in these assays include cardiac fibroblasts, cardiac myocytes, skeletal myocytes, and human umbilical vein endothelial cells from primary cultures, among other cell types. Suitable established cell lines include: NIH 3T3 fibroblasts (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992), and LNCap.FGC adenocarcinoma cells (ATCC No. CRL-1740.) Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabeled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:4246, 1988). Markers for mesenchymal stem cells have not been well identified (Owen et al., *J. of Cell Sci.* 87:731–738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of myocytes, smooth muscle cells, osteoblasts, adipocytes, chrondrocytes and endothelial cells. Molecules of the present invention for example, may while stimulating proliferation or differentiation of cardiac myocytes, inhibit proliferation or differentiation of adipocytes, by virtue of the affect on their common precursor/stem cells. Thus molecules of the present invention may have use in inhibiting chondrosarcomas, atherosclerosis, restenosis and obesity.

Assays measuring differentiation include, for example, measuring cell markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference). Alternatively, zmse1 polypeptide itself can serve as an additional cell-surface marker associated with stage-specific expression of a tissue. As such, direct measurement of zmse1 polypeptide, or its loss of expression in a tissue as it differentiates, can serve as a marker for differentiation of tissues.

Similarly, direct measurement of zmse1 polypeptide, or its loss of expression in a tissue can be determined in a tissue or cells as they undergo tumor progression. As the Ras and Rho family, and their effectors are involved with increases in invasiveness and motility of cells, the gain or loss of expression of zmes1 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zmse1 expression. For example, appearance or disappearance of polypeptides that regulate cell motility can be used to aid diagnosis and prognosis of prostate cancer (Banyard, J. and Zetter, B. R., *Cancer and Metast. Rev.* 17:449–458, 1999). As an effector of cell motility, zmse1 gain or loss of expression may serve as a diagnostic for prostate and other cancers.

Zmse1 can also be used to identify inhibitors (antagonists) of its activity. Test compounds are added to the assays disclosed herein to identify compounds that inhibit the activity of zmse1. In addition to those assays disclosed herein, samples can be tested for inhibition of zmse 1 activity within a variety of assays designed to measure receptor binding or the stimulation/inhibition of zmse1-dependent cellular responses. For example, zmse1-expressing cell lines can be transfected with a reporter gene construct that is responsive to a zmse1-stimulated cellular pathway. Reporter gene constructs of this type are known in the art, and will generally comprise a zmse1-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263:9063–6; 1988 and Habener, *Molec. Endocrinol.* 4:1087–94; 1990. Hormone response elements are reviewed in Beato, *Cell* 56:335–44; 1989. Candidate compounds, solutions, mixtures or extracts are tested for the ability to inhibit the activity of zmse1 on the target cells as evidenced by a decrease in zmse1 stimulation of reporter gene expression. Assays of this type will detect compounds that directly block effectors that bind zmse1 (or proteins to which zmse1 is an effector), as well as compounds that block processes in the cellular pathway upstream or subsequent to receptor-ligand binding. In the alternative, compounds or other samples can be tested for direct blocking of zmse1 binding to receptor using zmse1 tagged with a detectable label (e.g., $^{125}$I, biotin, horseradish peroxidase, FITC, and the like). Within assays of this type, the ability of a test sample to inhibit the binding of labeled zmse1 to the receptor is indicative of inhibitory activity, which can be confirmed through secondary assays. Receptors used within binding assays may be cellular receptors or isolated, immobilized receptors.

A role for zmse1 in the induction of cell motility suggests a role in spermatogenesis, a process that is remarkably similar to the development of blood cells (hematopoiesis). Briefly, spermatogonia undergo a maturation process similar to the differentiation of hematopoietic stem cells. Moreover, in view of cell motility effects, zmse1 polypeptides, agonists and antagonists have enormous potential in both in vitro and in vivo applications. For example, cell motility and polypeptides associated therewith have been implicated as a critical determinants in prostate cancer metastasis (Banyard, J. and Zetter, B. R., *Cancer and Metast. Rev.* 17:449–458, 1999). As an effector of cell motility, zmse1 may serve as a diagnostic for such cancers, and zmse1polypeptides, agonists and antagonists have therapeutic potential to treat such diseases. Zmse1 polypeptides, agonists and antagonists may also prove useful in modulating spermatogenesis and thus aid in overcoming infertility, or as therapeutics or diagnostics for male reproductive cancers such as prostate and testicular cancers. Antagonists are useful as research reagents for characterizing sites of ligand-receptor interaction. In vivo, zmse1 polypeptides, agonists or antagonists may find application in the treatment of male infertility, reproductive cancers, or as a male contraceptive agents.

The zmse1 polypeptides, antagonists of agonists, of the present invention can also modulate sperm capacitation. Before reaching the oocyte or egg and initiating an egg-sperm interaction, the sperm must be activated. The sperm undergo a gradual capacitation, lasting up to 3 or 4 hours in vitro, during which the plasma membrane of the sperm head and the outer acrosomal membrane fuse to form vesicles that facilitate the release of acrosomal enzymes. The acrosomal membrane surrounds the acrosome or acrosomal cap which is located at the anterior end of the nucleus in the sperm head. In order for the sperm to fertilize egg the sperm must penetrate the oocyte. To enable this process the sperm must undergo acrosomal exocytosis, also known as the acrosomal reaction, and release the acrosomal enzymes in the vicinity of the oocyte. These enzymes enable the sperm to penetrate the various oocyte layers, (the cumulus oophorus, the corona radiata and the zona pellucida). The released acrosomal enzymes include hyaluronidase and proacrosin, in addition to other enzymes such as proteases. During the acrosomal reaction, proacrosin is converted to acrosin, the active form of the enzyme, which is required for and must occur before binding and penetration of the zona pellucida is possible. A combination of the acrosomal lytic enzymes and sperm tail movements allow the sperm to penetrate the oocyte layers. Numerous sperm must reach the egg and release acrosomal enzymes before the egg can finally be fertilized. Only one sperm will successfully bind to, penetrate and fertilize the egg, after which the zona hardens so that no other sperm can penetrate the egg (Zaneveld, in Male Infertility Chapter 11, Comhaire (Ed.), Chapman & Hall, London, 1996). Peptide hormones, such as insulin homologs are associated with sperm activation and egg-sperm interaction. For instance, capacitated sperm incubated with relaxin show an increased percentage of progressively motile sperm, increased zona penetration rates, and increased percentage of viable acrosome-reacted sperm (Carrell et al., *Endocr. Res.* 21:697–707, 1995). Similarity of the zmse1 polypeptide structure to signal transduction molecules and the potential of zmse1 effects on indirectly effecting cell-cell interaction in the testis, prostate and uterus suggests that the zmse1 polypeptides described herein play a role in these and other reproductive processes.

Accordingly, proteins of the present invention can have applications in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who have physiological or metabolic disorders preventing natural conception or can be used to enhance in vitro fertilization. Such methods are also used in animal breeding programs, such as for livestock breeding and could be used as methods for the creation of transgenic animals. Proteins of the present invention can be combined with sperm, an egg or an egg-sperm mixture prior to fertilization of the egg. In some species, sperm capacitate spontaneously during in vitro fertilization procedures, but normally sperm capacitate over an extended period of time both in vivo and in vitro. It is advantageous to increase sperm activation during such procedures to enhance the likelihood of successful fertilization. The washed sperm or sperm removed from the seminal plasma used in such assisted reproduction methods has been shown to have altered reproductive functions, in particular, reduced motility and zona interaction. To enhance fertilization during assisted reproduction methods sperm is capacitated using exogenously added compounds. Suspension of the sperm in seminal plasma from normal subjects or in a "capacitation media" containing a cocktail of compounds known to activate sperm, such as caffeine, dibutyl cyclic adenosine monophosphate (dbcAMP) or theophylline, have resulted in improved reproductive function of the sperm, in particular, sperm motility and zonae penetration (Park et al., *Am. J. Obstet. Gynecol.* 158:974–9, 1988; Vandevoort et al., Mol. Repro. Develop. 37:299–304, 1993; Vandevoort and Overstreet, *J. Androl.* 16:327–33, 1995). The presence of immunoreactive relaxin in vivo and in association with cryopreserved semen, was shown to significantly increase sperm motility (Juang et al., *Anim. Reprod. Sci.* 20:21–9, 1989; Juang et al., *Anim. Reprod. Sci.* 22:47–53, 1990). Porcine relaxin stimulated sperm motility in cryopreserved human sperm (Colon et al., *Fertil. Steril.* 46:1133–39, 1986; Lessing et al., *Fertil. Steril.* 44:406–9, 1985) and preserved ability of washed human sperm to penetrate cervical mucus in vitro (Brenner et al., *Fertil. Steril.* 42:92–6, 1984). Polypeptides of the present invention can used in such methods to enhance viability of cryopreserved sperm, enhance sperm motility and enhance fertilization, particularly in association with methods of assisted reproduction.

A zmse1 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the $F_c$ portions are disulfide bonded to each other and two non-Ig polypeptides are arrayed in closed proximity to each other. Fusions of this type can be used to affinity purify ligand or binding partners, as an in vitro assay tool, or a zmse1 ligand antagonist. For use in assays, the chimeras are bound to a support via the $F_c$ region and used in an ELISA format.

A zmse1 polypeptide can also be used for purification of ligand, biomolecular substrates, or other proteins or antibodies that bind it. The zmse1 polypeptide or a polypeptide fragment containing the zmse1 CRIB motif can be used. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be-configured in the form of a column, and fluids containing ligand, cell lysates, membrane preparations, or lipid preparations, are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. N.Y. Acad. Sci.* 51: 660–72, 1949) and calorimetric assays (Cunningham et al., *Science* 253:54548, 1991; Cunningham et al., *Science* 245:821–25, 1991).

Zmse1 polypeptides can also be used to prepare antibodies that bind to zmse1 epitopes, peptides or polypeptides. The zmse1 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zmse1 polypeptide (e.g., SEQ ID NO:2). Polypeptides comprising a larger portion of a zmse1 polypeptide, i.e., from 30 to 10 residues up to the entire length of the amino acid sequence are included. Antigens or immunogenic epitopes can also include attached tags, adjuvants and carriers, as described herein. Suitable antigens include the zmse1 polypeptide encoded by SEQ ID NO:2 from amino acid number 1 (Met) to amino acid number 356 (Val), or a contiguous 13 to 343 amino acid fragment thereof. Other suitable antigens include the CRIB motif, N-terminal domain, variable C-terminal domain, and C-terminal tail as disclosed herein. Preferred peptides to use as antigens are hydrophilic peptides such as those predicted by one of skill in the art from a hydrophobicity plot, determined, for example, from a Hopp/Woods hydrophilicity profile based on a sliding six-residue window, with buried G, S, and T residues and exposed H, Y, and W residues ignored (See, FIG. 1). Zmse1 hydrophilic peptides include peptides comprising amino acid sequences selected from the group consisting of: (1) amino acid number 96 (Glu) to amino acid number 101 (Asp) of SEQ ID NO:2; (2) amino acid number 226 (Asp) to amino acid number 231 (Asp) of SEQ ID NO:2; (3) amino acid number 346 (Met) to amino acid number 351 (Glu) of SEQ ID NO:2; (4) amino acid number 347 (Asp) to amino acid number 352 (Asp) of SEQ ID NO:2; and (5) amino acid number 348 (Glu) to amino acid number 353 (Glu) of SEQ ID NO:2. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zmse1 polypeptide or a fragment thereof. The immunogenicity of a zmse1 polypeptide may be increased through the use of an adjuvant, such as alum (aluminum hydroxide) or Freund's complete or incomplete adjuvant. Polypeptides useful for immunization also include fusion polypeptides, such as fusions of zmse1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with known related polypeptide molecules. A threshold level of binding is determined if anti-zmse1 antibodies herein bind to a zmse1 polypeptide, peptide or epitope with an affinity at least 10-fold greater than the binding affinity to control (non-zmse1) polypeptide. It is preferred that the antibodies exhibit a binding affinity ($K_a$) of $10^6$ $M^{-1}$ or greater, preferably 10 $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Whether anti-zmse 1 antibodies do not significantly cross-react with known related polypeptide molecules is shown, for example, by the antibody detecting zmse1 polypeptide but not known related polypeptides using a standard Western blot analysis (Ausubel et al., ibid.). Examples of known related polypeptides are those disclosed in the prior art, such as known orthologs, and paralogs, and similar known members of a protein family, Screening can also be done using non-human zmse1, and zmse1 mutant polypeptides. Moreover, antibodies can be "screened against" known related polypeptides, to isolate a population that specifically binds to the zmse1 polypeptides. For example, antibodies raised to zmse1 are adsorbed to related polypeptides adhered to insoluble matrix; antibodies specific to zmse1 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984. Specifically binding anti-zmse1 antibodies can be detected by a number of methods in the art, and disclosed below.

A variety of assays known to those skilled in the art can be utilized to detect antibodies which bind to zmse1 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zmse1 protein or polypeptide.

Alternative techniques for generating or selecting antibodies useful herein include in vitro exposure of lymphocytes to zmse1 protein or peptide, and selection of antibody display libraries in phage or similar vectors (for instance, through use of immobilized or labeled zmse1 protein or peptide). Genes encoding polypeptides having potential zmse1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zmse1 sequences disclosed herein to identify proteins which bind to zmse1. These "binding polypeptides" which interact with zmse1 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor. The binding polypeptides can also be used for diagnostic assays for determining circulating levels of zmse1 polypeptides; for detecting or quantitating soluble zmse1 polypeptides as marker of underlying pathology or disease. These binding polypeptides can also act as zmse1 "antagonists" to block zmse1 binding and signal transduction in vitro and in vivo. These anti-zmse1 binding polypeptides would be useful for inhibiting zmse1 activity or protein-binding.

Antibodies to zmse1 may be used for tagging cells that express zmse1; for isolating zmse1 by affinity purification; for diagnostic assays for determining circulating levels of zmse1 polypeptides; for detecting or quantitating soluble zmse1 as marker of underlying pathology or disease; in analytical methods employing FACS; for screening expression libraries; for generating anti-idiotypic antibodies; and as neutralizing antibodies or as antagonists to block zmse1 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zmse1 or fragments thereof may be used in vitro to detect denatured zmse1 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zmse1 polypeptides or anti-zmse1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zmse1-cytokine fusion proteins or antibody-cytokine fusion proteins can be used for enhancing in vivo killing of target tissues (for example, blood, bone marrow or other cancers), if the zmse 1 polypeptide or anti-zmse 1 antibody targets the hyperproliferative blood or bone marrow cell (See, generally, Hornick et al., *Blood* 89:4437–47, 1997). Hornick et al. described fusion proteins that enable targeting of a cytokine to a desired site of action, thereby providing an elevated local concentration of cytokine. Suitable zmse1 polypeptides or anti-zmse1 antibodies can target an undesirable cell or tissue (i.e., a tumor or a leukemia), and the fused cytokine mediate improved target cell lysis by effector cells. Suitable cytokines for this purpose include interleukin 2 and granulocyte-macrophage colony-stimulating factor (GM-CSF), for instance.

In yet another embodiment, if the zmse1 polypeptide or anti- zmse1 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein. The bioactive polypeptide or antibody conjugates described herein can be delivered intravenously, intraarterially or intraductally, or may be introduced locally at the intended site of action.

The polypeptides, antagonists, agonists, nucleic acid antibodies of the present invention can be used in treatment of disorders associated with cancer, metastasis, vasoconstriction, heart arrhythmia, heart inflammation, congestive heart disease, muscle spasms and fatigue, inflammation, testicular function, fertility, birth control, and the like. The molecules of the present invention can be used to modulate contractility or inflammation or to treat or prevent development of pathological conditions in diverse tissues. In particular, certain syndromes/diseases may be amenable to such diagnosis, treatment or prevention.

Diagnostic methods of the present invention involve the detection of zmse1 polypeptides in the serum or tissue biopsy of a patient undergoing analysis of heart, spleen, testicular or muscle function or evaluation for possible cancers. Such polypeptides can be detected using immunoassay techniques and antibodies, described herein, that are capable of recognizing polypeptide epitopes. More specifically, the present invention contemplates methods for detecting zmse1 polypeptides comprising:

exposing a test sample potentially containing zmse1 polypeptides to an antibody attached to a solid support, wherein said antibody binds to a first epitope of a zmse1 polypeptide;

washing the immobilized antibody-polypeptide to remove unbound contaminants;

exposing the immobilized antibody-polypeptide to a second antibody directed to a second epitope of a zmse1 polypeptide, wherein the second antibody is associated with a detectable label; and detecting the detectable label. Altered levels of zmse1 polypeptides in a test sample, such as serum sweat, saliva, biopsy, tumor biopsy, and the like, can be monitored as an indication of heart, spleen, testicular or muscle function or of cancer, invasion or metastasis or other disease, when compared against a normal control.

Additional methods using probes or primers derived, for example, from the nucleotide sequences disclosed herein can also be used to detect zmse1 expression in a patient sample, such as a blood, saliva, sweat, tissue sample, or the like. For example, probes can be hybridized to tumor tissues and the hybridized complex detected by in situ hybridization. Zmse1 sequences can also be detected by PCR amplification using cDNA generated by reverse translation of sample mRNA as a template (*PCR Primer A Laboratory Manual*, Dieffenbach and Dveksler, eds., Cold Spring Harbor Press, 1995). When compared with a normal control, both increases or decreases of zmse1 expression in a patient sample, relative to that of a control, can be monitored and used as an indicator or diagnostic for disease.

Polynucleotides encoding zmse1 polypeptides are useful within gene therapy applications where it is desired to increase or inhibit zmse1 activity. For example, in disease states where cell migration or motility is impaired or deficient, introduction of a zmse1 gene could be used as a therapeutic. If a mammal has a mutated or absent zmse1 gene, the zmse1 gene can be introduced into the cells of the mammal. In one embodiment, a gene encoding a zmse1 polypeptide is introduced in vivo in a viral vector. Such vectors include an attenuated or defective DNA virus, such as, but not limited to, herpes simplex virus (HSV), retroviruses, papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zmse1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zmse1 gene transcription, such as to inhibit cell proliferation in vivo. Polynucleotides that are complementary to a segment of a zmse1-encoding polynucleotide (e.g., a polynucleotide as set forth in SEQ ID NO:1) are designed to bind to zmse1-encoding mRNA and to inhibit translation of such mRNA. Such antisense polynucleotides are used to inhibit expression of zmse1 polypeptide-encoding genes in cell culture or in a subject.

The present invention also provides reagents which will find use in diagnostic applications. For example, the zmse1 gene, a probe comprising zmse1 DNA or RNA or a subsequence thereof can be used to determine if the zmse1 gene is present on chromosome 17 or if a mutation has occurred. Zmse1 is located at the 17q24.1 region of chromosome 17 (see, Example 3). Detectable chromosomal aberrations at the zmse1 gene locus include, but are not limited to, aneuploidy, gene copy number changes, translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

The precise knowledge of a gene's position can be useful for a number of purposes, including:1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zmse1 gene is located at the 17q24.1 region of chromosome 17. Several genes of known function map to this region. Moreover, one of skill in the art would recognize that the 7q24 region is involved in several cancers, and that translocations, loss of heterogeneity (LOH) and other chromosomal abnormalities are often found in cancers. Thus, a marker in the 17q24.1 locus, such as provided by the polynucleotides of the present invention, would be useful in detecting translocations, aneuploidy, rearrangements, LOH other chromosomal abnormalities involving this region that are present in cancers. For example, zmse1 polynucleotide probes can be used to detect abnormalities or genotypes associated with the cancer susceptibility marker BRCA1, localized to 17q21, which is associated with breast, ovarian and prostate cancers (Hall, J. M. et al., *Science* 250:1684–1689, 1990). Zmse1 is localized to the 17q24.1, is likely a Rho family effector, and could also be directly involved in breast cancer or other tumors. Moreover, there is evidence for cancer resulting from mutations in the 17q24 region: the somatostatin receptor 2 gene (17q24) may be associated with cancers, such as small cell lung cancer (Zhang, C.-Y. et al., *Biochem. Biophys. Res. Commun.*

210:805–815, 1995); and esophageal cancers (Hennies, H.-C. et al., *Genomics* 29:537–540, 1995).

Moreover, zmse1 polynucleotide probes can be used to detect abnormalities or genotypes associated with pituitary and placental human growth hormone (GH), which maps to the 17q22-q24 region of chromosome 17. Mutations and deletions in the GH gene can create GH deficiencies and other diseases in humans, and such a diagnostic could assist physicians in determining the type of GH disease and appropriate associated therapy. As such, use of inventive anti-zmse1 antibodies, polynucleotides, and polypeptides can be used for the detection of zmse1 polypeptide, mRNA or anti-zmse1 antibodies, thus serving as markers and be directly used for detecting or diagnosing growth hormone deficiencies or cancers using methods known in the art and described herein. For example, zmse1 can be used to detect abnormalities or genotypes associated with the cyclin-dependent kinase 3 (CDK3) gene, involved in controlling cell cycle and intracellular signaling, maps to 17q22-qter, and is likely involved in human cancer (Bullrich, F. et al., *Cancer Res.* 55:1199–1205, 1995). Moreover, Zmse1 polynucleotide probes can be used to detect abnormalities or genotypes associated with dipeptidyl carboxypeptidase 1 (DCP1) (17q23), also known as Angiotensin I Converting Enzyme (ACE1), such as those that are implicated in heart disease, hypertension and male infertility (for example., see, Arbustini, E. et al., *Brit. Heart J.* 74:584–591, 1995; Cambien, F. et al., *Nature* 359:641–644, 1992; and Hagaman, J. R. et al., *Proc. Natl. Acad. Sci.* 95:2552–2557. 1998). Further, zmse1 polynucleotide probes can be used to detect abnormalities or genotypes associated with chromosome 17q24 deletions and translocations associated with human diseases, such as in the myeloperoxidase locus (17q23.1), or in cancers. Moreover, amongst other genetic loci, those for myeloperoxidase deficiency, (17q23.1), loci associated with cataracts (17q24), defects in'sodium channel voltage-gated type 2 (resulting in several different syndromes) (17q23.1-q25.3), all manifest themselves in human disease states as well as map to this region of the human genome. See the Online Mendellian Inheritance of Man (OMIM) gene map, and references therein, for this region of chromosome 17 on a publicly available WWW server NIH-Bethesda, Md. All of these serve as possible candidate genes for an inheritable disease which show linkage to the same chromosomal region as the zmse1 gene. Thus, zmse1 polynucleotide probes can be used to detect abnormalities or genotypes associated with these defects.

Similarly, defects in the zmse1 gene itself may result in a heritable human disease state. Molecules of the present invention, such as the polypeptides, antagonists, agonists, polynucleotides and antibodies of the present invention would aid in the detection, diagnosis prevention, and treatment associated with a zmse1 genetic defect.

A diagnostic could assist physicians in determining the type of disease and appropriate associated therapy, or assistance in genetic counseling or diagnosing cancer. As such, the inventive anti-zmse1 antibodies, polynucleotides, and polypeptides can be used for the detection of zmse1 polypeptide, mRNA or anti-zmse1 antibodies, thus serving as markers and be directly used for detecting or genetic diseases or cancers, as described herein, using methods known in the art and described herein. Further, zmse1 polynucleotide probes can be used to detect abnormalities or genotypes associated with chromosome 17q24.1 deletions and translocations associated with human diseases, such as those described above, or other translocations involved with malignant progression of tumors or other 17q24.1 mutations, which are expected to be involved in chromosome rearrangements in malignancy; or in other cancers. Similarly, zmse1 polynucleotide probes can be used to detect abnormalities or genotypes associated with chromosome 17q24.1 trisomy and chromosome loss associated with human diseases or spontaneous abortion. Thus, zmse1 polynucleotide probes can be used to detect abnormalities or genotypes associated with these defects.

As discussed above, defects in the zmse1 gene itself may result in a heritable human disease state. Molecules of the present invention, such as the polypeptides, antagonists, agonists, polynucleotides and antibodies of the present invention would aid in the detection, diagnosis prevention, and treatment associated with a zmse1 genetic defect. In addition, zmse1 polynucleotide probes can be used to detect allelic differences between diseased or non-diseased individuals at the zmse1 chromosomal locus. As such, the zmse1 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14–17 nt). PCR primers are at least 5 nt in length, preferably 15 or more, more preferably 20–30 nt. For gross analysis of genes, or chromosomal DNA, a zmse1 polynucleotide probe may comprise an entire exon or more. Exons are readily determined by one of skill in the art by comparing zmse1 sequences (SEQ ID NO:1) with the human genomic DNA for zmse1 (Genbank Accession No. AC026091). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zmse1 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zmse 1 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zmse1 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zmse1 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)). Direct analysis of an zmse1 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the zmse1 gene, referred to as "transgenic mice," and mice that exhibit a complete absence of zmse1 gene function, referred to as "knockout mice," may also be generated (Snouwaert et al., *Science* 257:1083, 1992; Lowell et al., *Nature* 366:740–42, 1993; Capecchi, M. R., *Science* 244: 1288–1292, 1989; Palmiter, R. D. et al. *Annu Rev Genet*. 20: 465–499, 1986). For example, transgenic mice that over-express zmse1, either ubiquitously or under a tissue-specific or tissue-restricted promoter can be used to ask whether over-expression causes a phenotype. For example, over-expression of a wild-type zmse1 polypeptide, polypeptide fragment or a mutant thereof may alter normal cellular processes, resulting in a phenotype that identifies a tissue in which zmse1 expression is functionally relevant and may indicate a therapeutic target for the zmse1, its agonists or antagonists. For example, a preferred transgenic mouse to engineer is one that over-expresses the full length human zmse1 polypeptide (residue 1 (Met) to residue 356 (Val) of SEQ ID NO:2); or more preferably the full length mouse zmse1 polypeptide (residue 1 (Met) to residue 349 (Val) of SEQ ID NO:5). Preferred tissue-specific or tissue-restricted promoters include lymphoid-restricted, epithelial-specific, colon-specific, ovary-specific and skin-restricted promoters. Moreover, such over-expression may result in a phenotype that shows similarity with human diseases. Similarly, knockout zmse1 mice can be used to determine where zmse1 is absolutely required in vivo. A transgenic mouse that is a knockout mouse would not expresses residue 1 (Met) to residue 349 (Val) of SEQ ID NO:5, because they would exhibit a complete absence of endogenous zmse1 gene function. The phenotype of knockout mice is predictive of the in vivo effects of that a zmse1 antagonist, such as those described herein, may have. The murine zmse1 mRNA, and cDNA is isolated (SEQ ID NO:4) and can be used to isolate mouse zmse 1 genomic DNA (Genbank Accession No. AC026091), which are subsequently used to generate knockout mice. These transgenic and knockout mice may be employed to study the zmse1 gene and the protein encoded thereby in an in vivo system, and can be used as in vivo models for corresponding human or animal diseases (such as those in commercially viable animal populations). The mouse models of the present invention are particularly relevant as tumor models for the study of cancer biology and progression. Such models are useful in the development and efficacy of therapeutic molecules used in human cancers. Because increases in zmse1 expression, as well as decreases in zmse1 expression are associated with specific human cancers, both transgenic mice and knockout mice would serve as useful animal models for cancer. Moreover, in a preferred embodiment, zmse1 transgenic mouse can serve as an animal model for specific tumors, particularly colon cancer, ovarian cancer, leukemia or melanoma. Moreover, transgenic mice expression of zmse1 antisense polynucleotides or ribozymes directed against zmse1, described herein, can be used analogously to transgenic mice described above.

The invention is further illustrated by the following non-limiting examples.

EXAMPLES

Example 1

Isolation and Cloning of the Human Zmse1

A. Using an EST Sequence to Obtain Full-length Human Zmse1

Scanning of a translated human cDNA database resulted in identification of an expressed sequence tag (EST) sequence which was used to identify a human full length cDNA from a K562 cDNA library prepared in house (K562 cells; ATCC No. CCL-243).

Confirmation of the full length human cDNA sequence was made by sequence analyses of the cDNA from which the EST originated. This cDNA was contained in a plasmid. The human zmse1 cDNA clone was sequenced using the following primers: ZC18489 (SEQ ID NO:21), ZC18106 (SEQ ID NO:22), ZC18438 (SEQ ID NO:23), ZC18165 (SEQ ID NO:24), ZC18214 (SEQ ID NO:25), ZC18275 (SEQ ID NO:26), ZC18213 (SEQ ID NO:27), ZC18285 (SEQ ID NO:28), ZC18388 (SEQ ID NO:29), ZC18105 (SEQ ID NO:30), ZC18452 (SEQ ID NO:31), and vector primers ZC6,768 (SEQ ID NO:17), and ZC694. (SEQ ID NO:18). Sequencing results indicated a 3076 bp insert with a 1068 bp open reading frame beginning with an initiating Met and ending with a stop signal. The sequence analyses revealed that the cDNA encompassed the entire coding region of the DNA encoding human zmse1. The cDNA sequence is shown in SEQ ID NO:1 and the corresponding deduced polypeptide sequence is shown in SEQ ID NO:2.

Example 2

Tissue Distribution of Zmse1 in Human Tissues

A. Human Tissue Blots Probed with a Human zmse1 Probe

Northern blot analysis was performed using Human Multiple Tissue Blots (MTN I, MTN II, and MTN III) (Clontech, Palo Alto, Calif.). A full length human zmse1 probe, based directly on the zmse1 cDNA (Example 1) was generated by PCR. The PCR fragment was gel purified using QIAquick gel extraction kit (Qiagen, Santa Clarita, Calif.). The probe was radioactively labeled with $^{32}p$ using the Rediprime II DNA Labeling system (Amersham, UK) according to Manufacturer's specifications. The probe was purified using a Nuctrap push column (Stratagene cloning system, La Jolla, Calif.). Expresshyb (Clontech) solution was used for the hybridizing solution for the blots. Hybridization took place overnight at 65° C. The blots were then washed 4× in 2×SCC and 0.05% SDS at RT, followed by two washes in 0.1×SSC and 0.1% SDS at 50° C. One transcript size was detected at approximately 3.6 kb. Signal intensity was ubiquitous for those tissues tested.

A Dot Blot was also performed using Human RNA Master Blots™ (Clontech). The methods and conditions for the Dot Blot were the same as for the Multiple Tissue Blots disclosed above. Again, signal intensity was ubiquitous for those tissues tested.

Example 3

Chromosomal Assignment and Placement of Human Zmse1

Zmse1 was mapped to human chromosome 17 using the commercially available version of the "Stanford G3 Radiation Hybrid Mapping Panel" (Research Genetics, Inc., Huntsville, Ala.). The "Stanford G3 RH Panel" contains DNAs from each of 83 radiation hybrid clones of the whole human genome, plus two control DNAs (the RM donor and the A3 recipient). Stanford University, Palo Alto.

For the mapping of Zmse1 with the "Stanford G3 RH Panel", 20 µl reactions were set up in a 96-well microtiter plate (Stratagene, La Jolla, Calif.) and used in a "RoboCycler Gradient 96" thermal cycler (Stratagene). Each of the 85 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC18,859 (SEQ ID NO:7), 1 µl antisense primer, ZC18,860 (SEQ ID NO:8), 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and ddH20 for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 66° C. and 1 minute and 15 seconds extension at 72° C., followed by a final 1 cycle extension of 7 minutes at 72°C. The reactions were separated by electrophoresis on a 2% agarose gel.

The results showed linkage of Zmse1 to the human chromosome 17 framework marker SHGC-11717 with a LOD score of 15.36 and at a distance of 8.98 cR_10000 from the marker. The use of surrounding genes/markers positions Zmse1 in the 15 17q24.3-q25 chromosomal region.

Example 4

Isolation and Cloning of Murine Zmse1 Extension of EST Sequence

Scanning of a translated DNA database using a protein sequence consisting of the translated open reading frame of human zmse1 as a query resulted in identification of EST1 166173, a murine expressed sequence tag (EST) found to be an ortholog of the human zmse1 (Example 1) (SEQ ID NO:1; SEQ ID NO:2). The mouse ortholog was designated muzmse 1.

Confirmation of the EST sequence was made by sequence analyses of the cDNA from which the EST originated. This cDNA was contained in a plasmid.

The mouse zmse1 cDNA clone was sequenced using the following primers: ZC19,115 (SEQ ID NO:9), ZC19,119 (SEQ ID NO:10), ZC19,190 (SEQ ID NO:11), ZC19,191 (SEQ ID NO:12), ZC19,192 (SEQ ID NO:13), ZC19,193 (SEQ ID NO:14), ZC19,278 (SEQ ID NO:15), ZC19,270 (SEQ ID NO:16), and vector primers ZC6,768 (SEQ ID NO:17), and ZC694. (SEQ ID NO:18). Sequencing results indicated a 2925 bp insert with a 1050 bp open reading frame beginning with an initiating Met and ending with a stop signal. The sequence analyses revealed that the cDNA encompassed the entire coding region of the DNA encoding muzmse1. The cDNA sequence is shown in SEQ ID NO:4 and the corresponding deduced polypeptide sequence is shown in SEQ ID NO:5.

Example 5

Generation of Untagged Zmse1 Recombinant Adenovirus

A. Preparation of DNA Construct for Generation of Adenovirus

The protein coding region of murine zmse1 was used to generate recombinant adenovirus. The 1050 bp mouse zmse1 cDNA was released from the TG12–8 vector (Example 6) using FseI and AscI enzymes. The cDNA was isolated on a 1% low melt SeaPlaque GTG™ (FMC, Rockland, Me.) gel and was then excised from the gel and the gel slice melted at 70° C., extracted twice with an equal volume of Tris buffered phenol, and EtOH precipitated. The DNA was resuspended in 10 µl $H_2O$.

The zmse1 cDNA was cloned into the FseI-AscI sites of pAdTrack CMV (He, T-C. et al., *PNAS* 95:2509–2514, 1998) in which the native polylinker was replaced with FseI, EcoRV, and AscI sites. Ligation was performed using the Fast-Link™ DNA ligation and screening kit (Epicentre Technologies, Madison, Wis.). In order to linearize the plasmid, approximately 5 µg of the pAdTrack™ CMV mouse zmse1 plasmid was digested with PmeI. Approximately 1 µg of the linearized plasmid was cotransformed with 200 ng of supercoiled pAdEasy™ (He et al., supra.) into BJ5183 cells. The co-transformation was done using a Bio-Rad Gene Pulser at 2.5kV, 200 ohms and 25 µF. The entire co-transformation was plated on 4 LB plates containing 25 µg/ml kanamycin. The smallest colonies were picked and expanded in LB/kanamycin and recombinant adenovirus DNA identified by standard DNA miniprep procedures. Digestion of the recombinant adenovirus DNA with FseI-AscI confirmed the presence of zmse1. The recombinant adenovirus miniprep DNA was transformed into DH10B competent cells and DNA prepared using a Qiagen maxi prep kit as per kit instructions.

B. Transfection of 293A Cells with Recombinant DNA

Approximately 5 µg of recombinant adenoviral DNA was digested with PacI enzyme (New England Biolabs) for 3 hours at 37° C. in a reaction volume of 100 µl containing 20–30 U of PacI. The digested DNA was extracted twice with an equal volume of phenol/chloroform and precipitated with ethanol. The DNA pellet was resuspended in 10 µl distilled water. A T25 flask of QBI-293A cells (Quantum Biotechnologies, Inc. Montreal, Qc. Canada), inoculated the day before and grown to 60–70% confluence, were transfected with the PacI digested DNA. The PacI-digested DNA was diluted up to a total volume of 50 μl with sterile HBS (150 mM NaCl, 20 mM HEPES). In a separate tube, 20 μl DOTAP (Boerhinger Mannheim, 1 mg/ml) was diluted to a total volume of 100 μl with HBS. The DNA was added to the DOTAP, mixed gently by pipeting up and down, and left at room temperature for 15 minutes.

The media was removed from the 293A cells and washed with 5 ml serum-free MEMalpha (Gibco BRL) containing 1 mM Sodium Pyruvate (GibcoBRL), 0.1 mM MEM non-essential amino acids (GibcoBRL) and 25mM HEPES buffer (GibcoBRL). 5 ml of serum-free MEM was added to the 293A cells and held at 37° C. The DNA/lipid mixture was added drop-wise to the T25 flask of 293A cells, mixed gently and incubated at 37° C. for 4 hours. After 4 h the media containing the DNA/lipid mixture was aspirated off and replaced with 5 ml complete MEM containing 5% fetal bovine serum. The transfected cells were monitored for Green Fluorescent Protein (GFP) expression and formation of foci, i.e., viral plaques.

Seven days after transfection of 293A cells with the recombinant adenoviral DNA, the cells expressed the GFP protein and started to form foci. These foci are viral "plaques" and the crude viral lysate was collected by using a cell scraper to detach all of the 293A cells. The lysate was transferred to a 50 ml conical tube. To release most of the virus particles from the cells, three freeze/thaw cycles were done in a dry ice/ethanol bath and a 37° water bath.

C. Amplification of Recombinant Adenovirus (rAdV)

The crude lysate was amplified (Primary (1°) amplification) to obtain a working "stock" of zmse1 rAdV lysate. Ten 10cm plates of nearly confluent (80–90%) 293A cells were set up 20 hours previously, 200 μl of crude rAdV lysate added to each 10 cm plate and monitored for 48 to 72 hours looking for CPE under the white light microscope and expression of GFP under the fluorescent microscope. When all of the 293A cells showed CPE (Cytopathic Effect) this 10 stock lysate was collected and freeze/thaw cycles performed as described under Crude rAdV Lysate.

Secondary (2°) Amplification of zmse1 rAdV was obtained as follows: Twenty 15 cm tissue culture dishes of 293A cells were prepared so that the cells were 80–90% confluent. All but 20 mls of 5%MEM media was removed and each dish was inoculated with 300–500 μl 1° amplified rAdv lysate. After 48 hours the 293A cells were lysed from virus production and this lysate was collected into 250 ml polypropylene centrifuge bottles and the rAdV purified.

D. AdV/cDNA Purification

NP-40 detergent was added to a final concentration of 0.5% to the bottles of crude lysate in order to lyse all cells. Bottles were placed on a rotating platform for 10 min. agitating as fast as possible without the bottles falling over. The debris was pelleted by centrifugation at 20,000×G for 15 minutes. The supernatant was transferred to 250 ml polycarbonate centrifuge bottles and 0.5 volumes of 20%PEG8000/2.5M NaCl solution added. The bottles were shaken overnight on ice. The bottles were centrifuged at 20,000×G for 15 minutes and supernatant discarded into a bleach solution. The white precipitate in two vertical lines along the wall of the bottle on either side of the spin mark is the precipitated virus/PEG. Using a sterile cell scraper, the precipitate from 2 bottles was resuspended in 2.5 ml PBS. The virus solution was placed in 2 ml microcentrifuge tubes and centrifuged at 14,000×G in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of CsCl added. The CsCl was dissolved and 1 ml of this solution weighed 1.34 g. The solution was transferred polycarbonate thick-walled centrifuge tubes 3.2 ml (Beckman #362305) and spin at 80,000 rpm (348,000×G) for 3–4 hours at 25° C. in a Beckman Optima TLX microultracentrifuge with the TLA-100.4 rotor. The virus formed a white band. Using wide-bore pipette tips, the virus band was collected.

The virus from the gradient has a large amount of CsCl which must be removed before it can be used on cells. Pharmacia PD-10 columns prepacked with Sephadex G-25M (Pharmacia) were used to desalt the virus preparation. The column was equilibrated with 20 ml of PBS. The virus was loaded and allowed it to run into the column. 5 ml of PBS was added to the column and fractions of 8–10 drops collected. The optical densities of 1:50 dilutions of each fraction was determined at 260 nm on a spectrophotometer. A clear absorbance peak was present between fractions 7–12. These fractions were pooled and the optical density (OD) of a 1:25 dilution determined. A formula is used to convert OD into virus concentration: (OD at 260 nm)(25) $(1.1 \times 10^{12})$=virions/ml. The OD of a 1:25 dilution of the zmse1 rAdV was 0.164, giving a virus concentration of $4.5 \times 10^{12}$ virions/ml.

To store the virus, glycerol was added to the purified virus to a final concentration of 15%, mixed gently but effectively, and stored in aliquots at −80° C.

E. Tissue Culture Infectious Dose at 50% CPE (TCID 50) Viral Titration Assay

A protocol developed by Quantum Biotechnologies, Inc. (Montreal, Qc.

Canada) was followed to measure recombinant virus infectivity. Briefly, two 96-well tissue culture plates were seeded with $1 \times 10^4$ 293A cells per well in MEM containing 2% fetal bovine serum for each recombinant virus to be assayed. After 24 hours 10-fold dilutions of each virus from $1 \times 10^{-2}$ to $1 \times 10^{-14}$ were made in MEM containing 2% fetal bovine serum. 100 μl of each dilution was placed in each of 20 wells. After 5 days at 37° C., wells were read either positive or negative for Cytopathic Effect (CPE) and a value for "Plaque Forming Units/ml " (PFU) is calculated.

$TCID_{50}$ formulation used was as per Quantum Biotechnologies, Inc., above. The titer (T) is determined from a plate where virus used is diluted from $10^{-2}$ to $10^{-14}$, and read 5 days after the infection. At each dilution a ratio (R) of positive wells for CPE per the total number of wells is determined.

To Calculate titer of the undiluted virus sample: the factor, "F"=1+d(S−0.5); where "S" is the sum of the ratios (R); and "d" is Log10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T).

The murine zmse1 adenovirus had a titer of $7.1 \times 10^{10}$ pfu/ml.

Example 6

Generation of Construct for Transgenic Expression of Mouse Zmse1 (Muzmse1)

Oligonucleotides were designed to generate a PCR fragment containing a consensus Kozak sequence and the mouse zmse1 coding region. These oligonucleotides were designed with an FseI site at the 5' end and an AscI site at the 3' end to facilitate cloning into pTG12-8, our standard transgenic vector. PMT12-8 contains the mouse MT-1 promoter and a 5' rat insulin II intron upstream of the FseI site.

PCR reactions were carried out with 200 ng mouse zmse1 template (Example 4) and oligonucleotides ZC19,514 (SEQ ID NO:19) and ZC19,515 (SEQ ID NO:20). PCR reaction conditions were as follows: one cycle at 95° C. for 5 minutes; followed by 15 cycles at 95° C. for 1 min., 58° C. for 1 min., and 72° C. for 1.0 min.; followed by 72° C. for 7 min.; followed by a 4° C. soak. PCR products were separated by agarose gel electrophoresis and purified using a QiaQuick™ (Qiagen) gel extraction kit. The isolated, 1050 bp, DNA fragment was digested with FseI and AscI (Boerhinger-Mannheim), phenol/chloroform extracted, ethanol precipitated, resuspended in TE, and ligated into pTG12-8 that was previously digested with FseI and AscI. The pTG12-8 plasmid, designed for expression of a gene of interest in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and grown in LB media containing 100 µg/ml ampicillin. Miniprep DNA was prepared from the picked clones and screened for the zmse1 insert by restriction digestion with EcoRI, and subsequent agarose gel electrophoresis. Maxipreps of the correct pTG-zmse1 construct were performed. A positive clone was sequenced to verify that the sequence was correct. A SalI fragment containing with 5' and 3' flanking sequences, the MT-1 promoter, the rat insulin H intron, zmse1 cDNA and the human growth hormone poly A sequence are prepared and to be used for microinjection into fertilized murine oocytes.

Qiagen Maxi Prep protocol (Qiagen) was used as per manufacturer's instruction to generate mumse1 DNA to use for further subcloning, for example, into adenovirus vectors described above (Example 5).

Example 7

Expression of Zmse1 in Cancer Tissues Using NCI60 Cancer Microarray

A. Determination of Genes Having Correlated Expression with Zmse1

Gene expression profile information for zmse1 was obtained from oligonucleotide and cDNA microarrays. Microarrays show the mRNA expression level of a large number of genes across a large number of cell types or cells exposed to various conditions, or cells in various replication steps, depending on the experiment. Because all of the information for all of the genes on any given microarray is obtained from the same biological experiment, and all biological experiments employing the same microarray provide results on the same set of genes, it is possible to compare the mRNA expression patterns of different genes to each other, as well as the expression pattern of a given gene in various tissues, cell lines, or cancers.

Briefly, microarray experiments are conducted by extracting the mRNA from reference tissues(s) or cell line(s) and from experimental sample tissue(s) or cell line(s). The reference mRNA is reverse transcribed to cDNA in a reaction along with a fluorescent dye label. The sample mRNA is likewise reverse transcribed to cDNA, but in the presence of a dye label with a different emission wavelength from the reference. The two cDNA samples are then mixed and hybridized to the microarray. The microarray itself has thousands of unlabeled cDNA clones covalently bound as spots (also called 'features') on its surface. The labeled cDNAs then bind to their respective microarray spots. If a particular gene is transcribed at a higher level in the experimental sample relative to the reference, then the spot will fluoresce to a greater degree in the experimental sample dye wavelength channel. Conversely, if the gene in the experimental sample is down regulated, then the wavelength channel of the reference dye will be stronger. Finally, the microarrays are scanned at the wavelengths of both dyes and the results for each spot are recorded and stored electronically. Large numbers of microarray experiments are typically done together using the same reference cDNA, but varying the experimental conditions, cell lines, tissues, time points, and the like.

Raw and/or processed microarray expression information was obtained from a subscription data set that was electronically downloaded. Publicly available, purchased, or in-house custom designed software can be used to analyze the microarray data (E.g., the publicly available NCI60 Cancer Microarray Project (Stanford University, Palo Alto, Calif.). Prior to analysis, spots were examined to exclude experimental artifacts (dust spots, substrate imperfections, incomplete or uneven hybridization washes, etc.) and absorbence was adjusted to take into account background fluorescence of the microarray substrate at both wavelengths. Very weak and very strong signals beyond the linear range response of the microarray reader were likewise excluded from analysis. Analyses were typically done on the ratio of the absorbance intensities of the reference and sample wavelength channels for each spot. These absorbance ratios were normalized to log base 2. Microarray information for zmse1 was found in Ross et al. using a 'NC160' microarray (Ross, D T et al., *Nature Genet.* 24:227–235, 2000). The reference mRNA was composed of a mixture of equal quantities of mRNA from HL-60, K562, NCI-H226, COLO 205, SNB-19, LOX-IMVI, OVCAR-3, OVCAR-4, CAKI-1, PC-3, MCF7, and Hs578T cells. See, Ross et al. supra. for details of this method.

A cDNA clone corresponding to the 3' end of zmse1 cDNA (and corresponding mRNA was included on the 'NCI60' microarray chip set (Ross et al. supra.). The zmse1 cDNA clone (IMAGE clone 486682; Incyte Pharmaceuticals, Palo Alto, Calif.; Genbank Accession No.'s AA044169 and AA044269) corresponds to zmse1 nucleotide positions 2435 to 3076 of SEQ ID NO:1. This chip set contained 9702 additional cloned cDNAs. Ross et al. performed 68 hybridization experiments with this chip set against 60 cancer cell lines. The data from the NCI60 microarray was purchased through the SUTECH™ Microarray Expression Database Subscription Program from Stanford Sequencing and Technology Center's Technology Development Group, (Stanford University, Palo Alto, Calif.).

Analysis was done by obtaining the Pearson correlation (R) between all pairs of spots in the entire set of microarray experiments. The Pearson correlation comprises a value from 1 to −1. A value of 1 shows that the expression in the two compared spots are positively correlated (both either are increased or decreased). A value of −1 shows that the expression in the two compared spots are negatively correlated (when one goes up, the other goes down, or visa versa). A value of 0 shows that the items are not correlated over the range of experiments. Although values between 0 and 1, or 0 and −1 can be considered positively or negatively correlated respectively, in the current analysis, correlations greater than 0.5 or less than −0.5 were considered to be significant. A similar analysis was performed by Ross et al, supra. Their results were also queried electronically by the NCI60 Cancer Microarray Project (Stanford University, Palo Alto, Calif.) world-wide-web resource. Thus genes potentially co-regulated or coexpressed with zmse1 were evaluated.

Table 5 shows the results of correlated cDNA clones in the NC160 microarray that have a Pearson's R correlation of expression greater than 0.5 or less than −0.5 with a zmse1 expithelial cytoskeletal proteins such as paxillin, uroplakin, and zonaula occludens protein. It also showed co-expression with the nucleotide metabolism gene, cytosolic hydroxymethyltransferase, and a negative correlation with adenylosuccinate lyase. Examination of the results obtained by our analysis, in conjunction with the results obtained from Stanford Genomic Resources (Stanford University, Palo Alto, Calif.) reveals that zmse1 is coexpressed with several cytoskeletal and cell-junction genes: cytoskeletal protein (HCYT), tight junction (zonula occludens) protein ZO-1, LIM domain protein (CLP), syndecan-1, SH3 binding protein, amphiglycan, and paxillin. These results showing that zmse1 is co-expressed with cytoskeletal proteins strongly reinforces that zmse1 is involved in cytoskeletal organization as described herein. Additionally, zmse1 expression is correlated with cytosolic serine hydroxymethyltransferase and cdc2L1, and anti-correlated with adenylosuccinate lyase, DNA-directed polymerase II, and cdc25A. These results likewise suggest that zmse1 has a role in cell cycle control and cancer.

TABLE 5

| Genbank Accession No. | Pearson's R | Description |
| --- | --- | --- |
| W46185 | 0.623538 | unknown |
| W30779-N94432 | 0.621390 | cytoskeletal protein (HCYT) |
| R79559-R79560 | 0.592573 | tight junction (zonula occludens) protein ZO-1 |
| AA053648-AA053259 | 0.557682 | cytosolic serine hydroxymethyltransferase |
| N47464-N47465 | 0.549652 | unknown |
| R99701-R99596 | 0.545722 | unknown |
| W81425 | 0.543336 | LIM domain protein (CLP) |
| R01486-R00830 | 0.532809 | syndecan-1 |
| W94188-W74616 | 0.524556 | breast tumor-associated protein |
| AA031793-AA031660 | 0.524266 | serine/threonine kinase, NEK4a |
| AA024925-AA024819 | 0.522498 | protein tyrosine phosphatase, LAR |
| T39472-T40608 | 0.519872 | SH3 binding protein |
| R53149-R53062 | 0.518507 | unknown |
| AA043212-AA043213 | 0.517950 | HREV 107-like protein |
| R09663-R09550 | 0.512873 | amphiglycan |
| N50356-N51577 | 0.512019 | unknown |
| W31174-N98734 | 0.510772 | unknown |
| AA047159-AA047298 | 0.509458 | unknown |
| W73440-W73379 | 0.509449 | unknown |
| H24396 | 0.507807 | unknown |
| AA034388-AA034389 | 0.507472 | immunogenic prostate tumor protein |
| AA011515-AA011682 | 0.504750 | unknown |
| W44684-W44685 | 0.504525 | maguk p55 subfamily member 3 (mpp3 protein) |
| AA040884-AA040885 | 0.503192 | calcyclin |
| W38993-N93209 | 0.502568 | T84 colon carcinoma cell IL-1beta regulated HSCC1 |
| AA004976-AA004863 | 0.500155 | Na,K-ATPase beta subunit (ATP1B) |
| N77727-N58359 | −0.501752 | RNA-associated protein-8 (RNAAP-8) |
| N41802-N32849 | −0.508249 | unknown |
| W95242-W95124 | −0.508527 | neuroblastoma apoptosis-related RNA binding protein (NAPOR-1) |
| W24524-N92340 | −0.511351 | MLC-1V/Sb isoform |
| AA052965 | −0.511973 | bone marrow protein BM034 |
| AA057262-AA058707 | −0.513009 | unknown |
| AA043037-AA042937 | −0.513606 | unknown |
| H59306-H59260 | −0.518568 | cdc2SA |
| N80399-N67978 | −0.527630 | unknown |
| W79319-W79419 | −0.533025 | DNA-directed polymerase II |
| AA010077 | −0.542907 | unknown |
| H99588 | −0.548033 | lymphoid nuclear protein (LAF4) |
| W92381-W92325 | −0.573708 | adenylosuccinate lyase (ADSL) | expression. Expressed genes are indexed by their accession number, and the corresponding protein, if known, is described.

Our analysis of the data showed that zmse1 had correlated expression (Pearson's R<−0.5 or >0.5) with 39 other cDNA clones (Table 5). The clones having correlated expression with zmse1 included cytoskeletal, cell cycle control, and other genes. For example, Zmse1 was coexpressed with B. Determination of Zmse1 Expression in Cell and Tissue Types, and Cancers Zmse1 expression in the microarray hybridization data described above was also analyzed for expression in various tissue types and cancers. Table 6 shows the Ratio of expression of zmse1 relative to the reference standard. The ratio of expression is another was to view the data. For each spot on the microarray, the ratio of fluorescence of the reference and sample wavelengths is a measure of the level of induction or repression of the test sample relative to the control (Ratio= [sample fluorescence/control reference fluorescence]). If there is no change in mRNA expression level of a given gene in the control and test samples, then the ratio for the corresponding spot will be 1. If the sample expression is induced in the test sample then the ratio of fluorescence for that spot will be greater than 1; if it is repressed then the ratio will be less than 1. The results indicated that zmse1 is up-regulated in colon cancer cell lines, and ovarian cancer cell lines. This data also indicated a down-regulation of zmse1 in leukemia and melanoma cancer cell lines. Prostate, CNS, renal, breast, and non small cell lung cancer cell lines generally showed mixed or weak changes in zmse1 expression relative to the control level. Zmse1 expression was highest in the LOX-IMVI (melanoma cell line), HOP-92 (non-small cell lung carcinoma cell line), BC2 (clinical sample of a lymph node metastasis of breast cancer), and COL0205 (colon cancer cell line). Zmse1 expression was lowest in the CCRF-CEM, RPMI-8226, MOLT-4 (leukemia cell lines), and the M-14 (melanoma cell line). These results show that a zmse1 increase or decrease in expression is correlated with certain human cancers. As such, detection of zmse1 expression increase or decrease can be used as a diagnostic for human cancers. Moreover, in a preferred embodiment, zmse1 can serve as a marker for certain tissue-specific tumors particularly colon cancer, ovarian cancer, leukemia or melanoma. Use of polynucleotides, polypeptides, and antibodies of the present invention for such diagnostic purposes are known in the art, and disclosed herein.

TABLE 6

| Cell Line or Tissue | Description | Ratio of Zmse 1 expression to reference |
|---|---|---|
| HS_578T | breast cancer cell line | 0.51 |
| MDA-N | breast cancer cell line | 0.59 |
| MDA-MB-435 | breast cancer cell line | 0.63 |
| BT-549 | breast cancer cell line | 0.8 |
| MDA-MB-231 | breast cancer cell line | 0.96 |
| MCF7 | breast cancer cell line | 1.15 |
| T-47D | breast cancer cell line | 1.57 |
| MCF7 | breast cancer cell line | 0.78 |
| MCF7 | breast cancer cell line | 1.13 |
| BC2 | breast cancer lymph node metastasis | 1 |
| BC16 | breast cancer tissue biopsy | 1.08 |
| BC2 | breast cancer tissue biopsy | 2.47 |
| Normal Breast | breast tissue biopsy, normal | 1.57 |
| SF-539 | CNS cancer cell line | 0.7 |
| SF-295 | CNS cancer cell line | 1 |
| SF-268 | CNS cancer cell line | 1.03 |
| SNB-19 | CNS cancer cell line | 1.15 |
| U251 | CNS cancer cell line | 1.22 |
| SW-620 | colon cancer cell line | 0.83 |
| HCT-15 | colon cancer cell line | 1.02 |
| KM12 | colon cancer cell line | 1.19 |

TABLE 6-continued

| Cell Line or Tissue | Description | Ratio of Zmse 1 expression to reference |
|---|---|---|
| HCT-116 | colon cancer cell line | 1.38 |
| HCC-2998 | colon cancer cell line | 1.42 |
| COLO205 | colon cancer cell line | 3.1 |
| HT-29 | colon cancer cell line | 1.13 |
| MOLT-4 | leukemia cell line | 0.16 |
| RPMI-8226 | leukemia cell line | 0.35 |
| CCRF-CEM | leukemia cell line | 0.43 |
| HL-60 | leukemia cell line | 0.52 |
| K-562 | leukemia cell line | 0.53 |
| SR | leukemia cell line | 0.98 |
| K562 | leukemia cell line | 0.61 |
| K562 | leukemia cell line | 0.62 |
| M-14 | melanoma cell line | 0.27 |
| SK-MEL-2 | melanoma cell line | 0.62 |
| SK-MEL-5 | melanoma cell line | 0.7 |
| SK-MEL-28 | melanoma cell line | 0.71 |
| UACC-257 | melanoma cell line | 0.71 |
| UACC-62 | melanoma cell line | 0.77 |
| MALME-3M | melanoma cell line | 0.89 |
| LOXIMVI | melanoma cell line | 1.86 |
| NCI-H23 | non-small cell lung cancer (NSCLC) cell line | 0.53 |
| NCI-H322 | NSCLC cell line | 0.69 |
| EKVX | NSCLC cell line | 0.74 |
| NCI-H522 | NSCLC cell line | 0.82 |
| NCI-H460 | NSCLC cell line | 1 |
| A549 | NSCLC cell line | 1.08 |
| HOP-62 | NSCLC cell line | 1.12 |
| NCI-H226 | NSCLC cell line | 1.29 |
| HOP-92 | NSCLC cell line | 2.31 |
| OVCAR-4 | ovarian cancer cell line | 0.73 |
| OVCAR-3 | ovarian cancer cell line | 1.04 |
| OVCAR-8 | ovarian cancer cell line | 1.04 |
| OVCAR-5 | ovarian cancer cell line | 1.35 |
| IGROV1 | ovarian cancer cell line | 1.39 |
| SK-OV-3 | ovarian cancer cell line | 1.49 |
| DU-145 | prostate cancer cell line | 1.1 |
| PC-3 | prostate cancer cell line | 1.19 |
| UO-31 | renal cancer cell line | 0.61 |
| RXF-393 | renal cancer cell line | 0.81 |
| SNB-75 | renal cancer cell line | 1 |
| 786-0 | renal cancer cell line | 1.06 |
| SN12C | renal cancer cell line | 1.06 |
| CAKI-1 | renal cancer cell line | 1.09 |
| ACHN | renal cancer cell line | 1.17 |
| A498 | renal cancer cell line | 1.34 |
| TK-10 | renal cancer cell line | 1.38 |
| ADR-RES | unknown | 1.28 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide from the group consisting of:
   (a) a polynucleotide sequence as shown in SEQ ID NO:1 from nucleotide 199 to nucleotide 639;
   (b) a polynucleotide sequence as shown in SEQ ID NO:1 from nucleotide 640 to nucleotide 1206;
   (c) a polynucleotide sequence as shown in SEQ ID NO:1 from nucleotide 640 to nucleotide 1266; and
   (d) a polynucleotide sequence as shown in SEQ ID NO:1 from nucleotide 199 to nucleotide 1266.

2. A vector comprising the following operably linked elements:
   a transcription promoter;
   a DNA segment comprising a polynucleotide selected from the group consisting of:
   (a) a polynucleotide sequence as shown in SEQ ID NO:1 from nucleotide 199 to nucleotide 639;
   (b) a polynucleotide sequence as shown in SEQ ID NO:1 from nucleotide 640 to nucleotide 1206;
   (c) a polynucleotide sequence as shown in SEQ ID NO:1 from nucleotide 640 to nucleotide 1266; and
   (d) a polynucleotide sequence as shown in SEQ ID NO:1 from nucleotide 199 to nucleotide 1266; and
   a transcription terminator,
   wherein the promoter is operably linked to the DNA segment, and the DNA segment is operably linked to the transcription terminator.

3. An isolated cell comprising the vector according to claim 2.

4. An isolated polynucleotide that encodes a polypeptide that comprises a sequence of amino acid residues selected from the group consisting of:
   (a) the amino acid sequence as shown in SEQ ID NO:2 from amino acid number 1 (Met), to amino acid number 147 (Ala);

(b) the amino acid sequence as shown in SEQ ID NO:2 from amino acid number 148 (Asn), to amino acid number 336 (Ser);

(c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val).

5. The isolated polynucleotide sequence according to claim 4, wherein the polynucleotide is selected from the group consisting of:

(a) a polynucleotide sequence as shown in SEQ ID NO:3 from nucleotide 1 to nucleotide 441;

(b) a polynucleotide sequence as shown in SEQ ID NO:3 from nucleotide 442 to nucleotide 1008;

(c) a polynucleotide sequence as shown in SEQ ID NO:3 from nucleotide 442 to nucleotide 1068; and (d) a polynucleotide sequence as shown in SEQ ID NO:3 from nucleotide 1 to nucleotide 1068.

6. The isolated polynucleotide according to claim 4, wherein the polynucleotide encodes a polypeptide that consists of a sequence of amino acid residues selected from the group consisting of:

(a) the amino acid sequence as shown in SEQ ID NO:2 from amino acid number 1 (Met), to amino acid number 147 (Ala);

(b) the amino acid sequence as shown in SEQ ID NO:2 from amino acid number 148 (Asn), to amino acid number 336 (Ser);

(c) the amino acid sequence as shown in SEQ ID NO:2 from amino acid number 148 (Asn), to amino acid number 356 (Ser); and (d) the amino acid sequence as shown in SEQ ID NO:2 from amino acid number 1 (Met), to amino acid number 356 (Val).

7. An expression vector comprising the following operably linked elements:

a transcription promoter;

a DNA segment encoding a polypeptide as shown in SEQ ID NO:2 from amino acid number 1 (Met), to amino acid number 356 (Val); and a transcription terminator, wherein the promoter is operably linked to the DNA segment, and the DNA segment is operably linked to the transcription terminator.

8. The expression vector according to claim 7, further comprising a secretory signal sequence operably linked to the DNA segment.

9. A cultured cell comprising the expression vector according to claim 7, wherein the cell expresses a polypeptide encoded by the DNA segment.

10. A method of producing a polypeptide comprising:

culturing the cell according to claim 9; and isolating the polypeptide produced by the cell.

11. A DNA construct encoding a fusion protein, the DNA construct comprising:

a first DNA segment encoding a polypeptide comprising a sequence of amino acid residues selected from the group consisting of:

(a) the amino acid sequence as shown in SEQ ID NO:2 from amino acid number 1 (Met), to amino acid number 147 (Ala);

(b) the amino acid sequence as shown in SEQ ID NO:2 from amino acid number 148 (Asn), to amino acid number 336 (Ser);

(c) the amino acid sequence as shown in SEQ ID NO:2 from amino acid number 148 (Asn), to amino acid number 356 (Ser);

(d) the amino acid sequence as shown in SEQ ID NO:2 from amino acid number 337 (Arg), to amino acid number 356 (Ser); and (e) the amino acid sequence as shown in SEQ ID NO:2 from amino acid number 1 (Met), to amino acid number 356 (Val); and at least one other DNA segment encoding an additional polypeptide, wherein the first and other DNA segments are connected in-frame; and wherein the first and other DNA segments encode the fusion protein.

12. An expression vector comprising the following operably linked elements:

a transcription promoter;

a DNA construct encoding the fusion protein according to claim 11; and a transcription terminator, wherein the promoter is operably linked to the DNA construct, and the DNA construct is operably linked to the transcription terminator.

13. A cultured cell comprising the expression vector according to claim 12, wherein the cell expresses a polypeptide encoded by the DNA construct.

14. A method of producing a fusion protein comprising:

culturing the cell according to claim 13; and isolating the polypeptide produced by the cell.

* * * * *

SEQUENCE LISTING

<160> NUMBER OF SEQ ID NOS: 31

<210> SEQ ID NO 1
<211> LENGTH: 3076
<212> TYPE: DNA
<213> ORGANISM: Homo sapiens

```
<220> FEATURE:
<221> NAME/KEY: CDS
<222> LOCATION: (199)...(1266)

<400> SEQUENCE: 1
gacaggggcc gccagcccct ccgccgcgcg gagcccacga aggggacagc gcagccggcc      60
cagagctcgg gtctccgggg accgagcctt atgatctcct cattgcgtcc ccctctgccc     120
actggacttg gacttcagat ctgaccccag acctgccggc tacctcggga gggcccacct     180
ccccgcccat ccagcaag atg cca atc ctc aag caa ctg gtg tcc agc tcg      231
                    Met Pro Ile Leu Lys Gln Leu Val Ser Ser Ser
                      1               5                  10 gtg cac tcc aag cgc cgt tcc cga gcg gac ctc acg gcc gag atg atc      279
Val His Ser Lys Arg Arg Ser Arg Ala Asp Leu Thr Ala Glu Met Ile
             15                  20                  25 agc gcc ccg ctg ggc gac ttc cgc cac acc atg cac gtt ggc cgg gcc      327
Ser Ala Pro Leu Gly Asp Phe Arg His Thr Met His Val Gly Arg Ala
         30                  35                  40 gga gac gcc ttt ggg gac acc tcc ttc ctc aat agc aag gct ggc gag      375
Gly Asp Ala Phe Gly Asp Thr Ser Phe Leu Asn Ser Lys Ala Gly Glu
 45                  50                  55 ccc gac ggc gag tcc ttg gac gaa cag ccc tct tct tca tct tcc aaa      423
Pro Asp Gly Glu Ser Leu Asp Glu Gln Pro Ser Ser Ser Ser Ser Lys
 60                  65                  70                  75 cgc agt ctc ctg tcc agg aag ttc cgg ggc agc aag cgg tca cag tcg      471
Arg Ser Leu Leu Ser Arg Lys Phe Arg Gly Ser Lys Arg Ser Gln Ser
                 80                  85                  90 gtg acc agg ggg gag cgg gag cag cgt gac atg ctg ggc tcc ctg cgg      519
Val Thr Arg Gly Glu Arg Glu Gln Arg Asp Met Leu Gly Ser Leu Arg
             95                 100                 105 gac tcg gcc ctg ttt gtc aag aat gcc atg tcc ctg ccc cag ctc aat      567
Asp Ser Ala Leu Phe Val Lys Asn Ala Met Ser Leu Pro Gln Leu Asn
        110                 115                 120 gag aag gag gcc gcg gag aag ggc acc agt aag ctg ccc aag agc ctg      615
Glu Lys Glu Ala Ala Glu Lys Gly Thr Ser Lys Leu Pro Lys Ser Leu
    125                 130                 135 tca tcc agc ccc gtg aag aag gcc aat gac ggg gag ggc ggc gat gag      663
Ser Ser Ser Pro Val Lys Lys Ala Asn Asp Gly Glu Gly Gly Asp Glu
140                 145                 150                 155 gag gcg ggc acg gag gag gca gtg ccc cgt cgg aat ggg gcc gcg ggt      711
Glu Ala Gly Thr Glu Glu Ala Val Pro Arg Arg Asn Gly Ala Ala Gly
                160                 165                 170 cca cat tcc cct gac ccc ctc ctc gat gag cag gcc ttt ggg gat ctg      759
Pro His Ser Pro Asp Pro Leu Leu Asp Glu Gln Ala Phe Gly Asp Leu
            175                 180                 185 aca gat ctg cct gtc gtg ccc aag gcc acg tac ggg ctg aag cat gcg      807
Thr Asp Leu Pro Val Val Pro Lys Ala Thr Tyr Gly Leu Lys His Ala
        190                 195                 200 gag tcc atc atg tcc ttc cac atc gac ctg ggg ccc tcc atg ctg ggt      855
Glu Ser Ile Met Ser Phe His Ile Asp Leu Gly Pro Ser Met Leu Gly
    205                 210                 215 gac gtc ctc agc atc atg gac aag gag gag tgg gac ccc gag gag ggg      903
Asp Val Leu Ser Ile Met Asp Lys Glu Glu Trp Asp Pro Glu Glu Gly
220                 225                 230                 235 gag ggt ggt tac cat ggc gat gag ggc gcc gct ggc acc atc acc cag      951
Glu Gly Gly Tyr His Gly Asp Glu Gly Ala Ala Gly Thr Ile Thr Gln
                240                 245                 250 gct ccc ccg tac gcc gtg gcg gcc cct ccc ctg gca agg cag gaa ggc      999
Ala Pro Pro Tyr Ala Val Ala Ala Pro Pro Leu Ala Arg Gln Glu Gly
            255                 260                 265
```

```
aag gct ggc cca gac ttg ccc tcc ctc ccc tcc cat gct ctg gag gat     1047
Lys Ala Gly Pro Asp Leu Pro Ser Leu Pro Ser His Ala Leu Glu Asp
            270                 275                 280 gag ggg tgg gca gca gcg gcc ccc agc ccc ggc tca gcc cgc agc atg     1095
Glu Gly Trp Ala Ala Ala Ala Pro Ser Pro Gly Ser Ala Arg Ser Met
        285                 290                 295 ggc agc cac acc aca cgg gac agc agc tcc ctc tcc agc tgc acc tca     1143
Gly Ser His Thr Thr Arg Asp Ser Ser Ser Leu Ser Ser Cys Thr Ser
300                 305                 310                 315 ggc atc ctg gag gag cgc agc cct gcc ttc cgg ggg ccg gac agg gcc     1191
Gly Ile Leu Glu Glu Arg Ser Pro Ala Phe Arg Gly Pro Asp Arg Ala
                320                 325                 330 cgg gct gct gtc tca aga cag cca gac aag gag ttc tcc ttc atg gat     1239
Arg Ala Ala Val Ser Arg Gln Pro Asp Lys Glu Phe Ser Phe Met Asp
                    335                 340                 345 gag gag gag gag gat gaa atc cgt gtg tgaggcggac agtgggtggc           1286
Glu Glu Glu Glu Asp Glu Ile Arg Val
            350                 355 caccgggagc tcttggctgc atcttctccc tgcccccacc ccactatgac ctttgaccct   1346
acggcgcagg ggcagccagg acccttgatt cagaccatgg accctggacc ttgtagatga   1406
gggacactgg cctggccctc gggtcttcgg aggacgtagg gggctggcat gggtgccgac   1466
tggctgcctg acttcatcat gctccctgca cttaggctgc gtgggacaag ggctgtgttg   1526
tcacagcagg aataggtttt cctctgttgg cctcccttc ctccaccctg gcctcaaatg    1586
gatgccagat gccaacccca gttctggcca cgtacagcca gcgggtcagc ccagaggcag   1646
cctcagctcc agggctaagg actctcggct cccattttct ctgctggcgt ttctgctgtg   1706
cccagcagtg gctgctgggg aagcagctgc agcaggaggg agacggtctt gcctctcagc   1766
ccctccctgc cccaccccag ctcctgccct ggaaatctgg agcccttgg agctgagctg    1826 gacgggggc cagctgcgag catgtgcact aaacgcagcc ctttccaggg gaagagaaca    1886
ggatggagaa tggaaggaaa gcccccagg cttcgtgaat tgcaagaagg gacccttcca    1946
ggatgacact aggaacaggg ctagggcact cgctcagtcc ctaggggctt gtttgttctt   2006
tattattgtg tttaaatcct tatagagcaa tatcaggatg gtgttaatag gtctgcctca   2066
gaatgagaat caatccttt agaaaacctt tatactaagc ctcctcttcg aaattcacag    2126 tgcgattag cggactggag tctggtggcg attagcggac tggagtctgg ggacatccgt    2186
ggcaaagaca ccagctcaac tttagtgctt cccaacttta tttagaatga catggggtgg   2246
gtgtctggtg tgtgtgtttt ccctacgcac ctcccatagc tattaacaac tgaggaaggc   2306
cagtgcagaa tattttgga gaacgatttt ttttttaaat aatatatcat tcctatgggg    2366
ggaaagcctt ttttttcttt ttggctgagt tattccctcc ctcccctcaa taccctcagt   2426
actgactact tccctttctt ttctcaggcc tcccccacc gacttttgag gccagggttg    2486
gccagattta gcaaaccaa aacagagtgc tgagttaaac gcaaatttca ggtaaacaaa    2546
agataatttt ctagcattaa tatgccccac gcaatatttg gaacacttat gtgaaaaatg   2606
atttgttttt ctgaaattca cgtttctctc tgagtcctgt aactgtcccc gagggattg    2666 agcagaagct cgggtatgag ccctgaggtt gactgccggt tattttttctg tcctgggaac  2726 agcctgaccc acctccctgt ctccatgtag ccagtgaggg gaggggagag cacagaacca   2786
accacagcca gggcgtccc catggcgact gtggcccggc cctcctctc ttgcctgact     2846 ctcctctctt gcctgactct agacactaac ttagttccag gttcggtgcc ctgttggtgc   2906
```

-continued

```
tcctgtttcc aatagcttag gtcccatggt gggggaggaa cctcagggc tatgcagccc    2966 ccgccagctg ccctcgaatc ccgtccaggc caattccaga ttctaaactg atttttttca   3026
tgatattgtc aaaacagtga ggaaacatta aaaaaaaaag ccctaaagca              3076
```

<210> SEQ ID NO 2
<211> LENGTH: 356
<212> TYPE: PRT
<213> ORGANISM: Homo sapiens

<400> SEQUENCE: 2

```
Met Pro Ile Leu Lys Gln Leu Val Ser Ser Val His Ser Lys Arg
 1               5                  10                  15

Arg Ser Arg Ala Asp Leu Thr Ala Glu Met Ile Ser Ala Pro Leu Gly
            20                  25                  30

Asp Phe Arg His Thr Met His Val Gly Arg Ala Gly Asp Ala Phe Gly
        35                  40                  45

Asp Thr Ser Phe Leu Asn Ser Lys Ala Gly Glu Pro Asp Gly Glu Ser
    50                  55                  60

Leu Asp Glu Gln Pro Ser Ser Ser Ser Lys Arg Ser Leu Leu Ser
65                  70                  75                  80

Arg Lys Phe Arg Gly Ser Lys Arg Ser Gln Ser Val Thr Arg Gly Glu
                85                  90                  95

Arg Glu Gln Arg Asp Met Leu Gly Ser Leu Arg Asp Ser Ala Leu Phe
            100                 105                 110

Val Lys Asn Ala Met Ser Leu Pro Gln Leu Asn Glu Lys Glu Ala Ala
        115                 120                 125

Glu Lys Gly Thr Ser Lys Leu Pro Lys Ser Leu Ser Ser Pro Val
    130                 135                 140

Lys Lys Ala Asn Asp Gly Glu Gly Gly Asp Glu Glu Ala Gly Thr Glu
145                 150                 155                 160

Glu Ala Val Pro Arg Arg Asn Gly Ala Ala Gly Pro His Ser Pro Asp
                165                 170                 175

Pro Leu Leu Asp Glu Gln Ala Phe Gly Asp Leu Thr Asp Leu Pro Val
            180                 185                 190

Val Pro Lys Ala Thr Tyr Gly Leu Lys His Ala Glu Ser Ile Met Ser
        195                 200                 205

Phe His Ile Asp Leu Gly Pro Ser Met Leu Gly Asp Val Leu Ser Ile
    210                 215                 220

Met Asp Lys Glu Glu Trp Asp Pro Glu Glu Gly Gly Gly Tyr His
225                 230                 235                 240

Gly Asp Glu Gly Ala Ala Gly Thr Ile Thr Gln Ala Pro Pro Tyr Ala
                245                 250                 255

Val Ala Ala Pro Pro Leu Ala Arg Gln Glu Gly Lys Ala Gly Pro Asp
            260                 265                 270

Leu Pro Ser Leu Pro Ser His Ala Leu Glu Asp Glu Gly Trp Ala Ala
        275                 280                 285

Ala Ala Pro Ser Pro Gly Ser Ala Arg Ser Met Gly Ser His Thr Thr
    290                 295                 300

Arg Asp Ser Ser Ser Leu Ser Cys Thr Ser Gly Ile Leu Glu Glu
305                 310                 315                 320

Arg Ser Pro Ala Phe Arg Gly Pro Asp Arg Ala Arg Ala Ala Val Ser
                325                 330                 335

Arg Gln Pro Asp Lys Glu Phe Ser Phe Met Asp Glu Glu Glu Asp
            340                 345                 350
```

```
                                       Glu Ile Arg Val
                                               355

<210> SEQ ID NO 3
<211> LENGTH: 1068
<212> TYPE: DNA
<213> ORGANISM: Artificial Sequence
<220> FEATURE:
<223> OTHER INFORMATION: Degenerate polynucleotide seuence for human
      zmse1
<221> NAME/KEY: misc_feature
<222> LOCATION: (1)...(1068)
<223> OTHER INFORMATION: n = A,T,C or G

<400> SEQUENCE: 3
atgccnathy tnaarcaryt ngtnwsnwsn wsngtncayw snaarmgnmg nwsnmgngcn      60
gayytnacng cngaratgat hwsngcnccn ytnggngayt tymgncayac natgcaygtn    120
ggnmgngcng gngaygcntt yggngayacn wsnttyytna aywsnaargc nggngarccn    180
gayggngarw snytngayga rcarccnwsn wsnwsnwsnw snaarmgnws nytnytnwsn    240
mgnaarttym gnggnwsnaa rmgnwsncar wsngtnacnm gnggngarmg ngarcarmgn    300
gayatgytng gnwsnytnmg ngaywsngcn ytnttygtna araaygcnat gwsnytnccn    360
carytnaayg araargargc ngcngaraar ggnacnwsna arytnccnaa rwsnytnwsn    420
wsnwsnccng tnaaraargc naaygayggn garggnggng aygargargc nggnacngar    480
gargcngtnc cnmgnmgnaa yggngcngcn ggnccncayw snccngaycc nytnytngay    540
garcargcnt tyggngayyt nacngayytn ccngtngtnc cnaargcnac ntayggnytn    600
aarcaygcng arwsnathat gwsnttycay athgayytng gnccnwsnat gytnggngay    660
gtnytnwsna thatggayaa rgargartgg gayccngarg argngargg nggntaycay    720 ggngaygarg gngcngcngg nacnathacn cargcnccnc cntaygcngt ngcgcnccn    780 ccnytngcnm gncargargg naargcnggn ccngayytnc cnwsnytncc nwsncaygcn    840
ytngargayg argngtgggc ngcngcngcn ccnwsnccng gnwsngcnmg nwsnatgggn    900
wsncayacna cnmgngayws nwsnwsnytn wsnwsntgya cnwsnggnat hytngargar    960
mgnwsnccng cnttymgngg nccngaymgn gcnmgngcng cngtnwsnmg ncarccngay   1020
aargarttyw snttyatgga ygargargar gargaygara thmgngtn                1068

<210> SEQ ID NO 4
<211> LENGTH: 2868
<212> TYPE: DNA
<213> ORGANISM: Mus musculus
<220> FEATURE:
<221> NAME/KEY: CDS
<222> LOCATION: (173)...(1219)

<400> SEQUENCE: 4
cgaggcgcca agcacaccga ggggagcgta cagccgcacc tggtctgcgc tcggggagct     60
ggggaccgag ccctctgatt gccctgtcta ccctttgcat tgctggactt cagatctgac   120
cccatacctg cctgttgcct tgggagtgcc cagctccccc gcagccagca cg atg ccc   178
                                                          Met Pro
                                                            1 att ctc aaa cag ctg gtg tcc agc tct gtg aac tcg aag cgc cgc tca   226
Ile Leu Lys Gln Leu Val Ser Ser Ser Val Asn Ser Lys Arg Arg Ser
            5                  10                  15 cgt gcg gac ctc aca gcc gag atg atc agt gcc ccg ctg ggt gac ttc   274
Arg Ala Asp Leu Thr Ala Glu Met Ile Ser Ala Pro Leu Gly Asp Phe
```

-continued

|  |  |
|---|---|
| cgc cac acc atg cat gtg ggc cgg gct ggg gac gcc ttt ggg gac acc<br>Arg His Thr Met His Val Gly Arg Ala Gly Asp Ala Phe Gly Asp Thr<br>35              40                  45                  50 | 322 |
| tcc ttc ctc act agc aag gcc agg gag gca gac gac gag tcc ctg gat<br>Ser Phe Leu Thr Ser Lys Ala Arg Glu Ala Asp Asp Glu Ser Leu Asp<br>            55                  60                  65 | 370 |
| gag cag gcc tcc gct tcc aag ctc agc ctc ctg tcc agg aag ttc cgg<br>Glu Gln Ala Ser Ala Ser Lys Leu Ser Leu Leu Ser Arg Lys Phe Arg<br>        70                  75                  80 | 418 |
| ggc agc aaa cgt tca cag tcc gtg acc aga ggg gac cgg gag cag aga<br>Gly Ser Lys Arg Ser Gln Ser Val Thr Arg Gly Asp Arg Glu Gln Arg<br>    85                  90                  95 | 466 |
| gac atg ctg ggc tcc ctg cgg gac tca gca ctg ttt gtc aag aat gcc<br>Asp Met Leu Gly Ser Leu Arg Asp Ser Ala Leu Phe Val Lys Asn Ala<br>100                 105                 110 | 514 |
| atg tcc ctg cct cag ctc aat gag aag gaa gcc gcg gag aag gac tcg<br>Met Ser Leu Pro Gln Leu Asn Glu Lys Glu Ala Ala Glu Lys Asp Ser<br>115             120                 125             130 | 562 |
| agc aag ctg ccc aag agc ctg tcg tcc agc cct gtg aag aag gca gac<br>Ser Lys Leu Pro Lys Ser Leu Ser Ser Ser Pro Val Lys Lys Ala Asp<br>            135                 140                 145 | 610 |
| gct aga gat ggt ggc ccg aag agt ccc cat cgg aac ggg gcc aca ggc<br>Ala Arg Asp Gly Gly Pro Lys Ser Pro His Arg Asn Gly Ala Thr Gly<br>        150                 155                 160 | 658 |
| ccc aac tca cct gac cca ctc ctt gac gag cag gcc ttt ggg gac ctg<br>Pro Asn Ser Pro Asp Pro Leu Leu Asp Glu Gln Ala Phe Gly Asp Leu<br>    165                 170                 175 | 706 |
| atg gat ctg ccc atc atg ccc aaa gtc agc tac ggg ctg aag cat gca<br>Met Asp Leu Pro Ile Met Pro Lys Val Ser Tyr Gly Leu Lys His Ala<br>180                 185                 190 | 754 |
| gag tcg atc ctg tcc ttc cac atc gac ctg ggg cct tcc atg ctg gga<br>Glu Ser Ile Leu Ser Phe His Ile Asp Leu Gly Pro Ser Met Leu Gly<br>195             200                 205             210 | 802 |
| gat gtt ctc agc atc atg gac aag gac cag tgg ggc tca gag gag gag<br>Asp Val Leu Ser Ile Met Asp Lys Asp Gln Trp Gly Ser Glu Glu Glu<br>            215                 220                 225 | 850 |
| gag gaa gct ggc ggg tac cgt gac aag gaa ggc ccc agc agc att gtc<br>Glu Glu Ala Gly Gly Tyr Arg Asp Lys Glu Gly Pro Ser Ser Ile Val<br>        230                 235                 240 | 898 |
| cag gca ccc cct gtg ctg gag gtg gtt cct cct cta ggg aga cag gaa<br>Gln Ala Pro Pro Val Leu Glu Val Val Pro Pro Leu Gly Arg Gln Glu<br>    245                 250                 255 | 946 |
| agc aag gcc agc tgg gac cag gcc tct atg ctg ccc ccc cac gct gtg<br>Ser Lys Ala Ser Trp Asp Gln Ala Ser Met Leu Pro Pro His Ala Val<br>260                 265                 270 | 994 |
| gag gat gac gga tgg gcg gtg gta gcc ccc agc ccc agc tca gca cgc<br>Glu Asp Asp Gly Trp Ala Val Val Ala Pro Ser Pro Ser Ser Ala Arg<br>275             280                 285             290 | 1042 |
| agt gtg ggc agc cac acc acg cgg gac agc agc tcc ctg tcc agc tac<br>Ser Val Gly Ser His Thr Thr Arg Asp Ser Ser Ser Leu Ser Ser Tyr<br>            295                 300                 305 | 1090 |
| acc tca ggc gtc ctt gag gag cgc agc cca gct ttc aga ggc cca gac<br>Thr Ser Gly Val Leu Glu Glu Arg Ser Pro Ala Phe Arg Gly Pro Asp<br>        310                 315                 320 | 1138 |
| agg gtg gca gct gct ccc cca agg cag cca gac aag gaa ttc tgc ttc<br>Arg Val Ala Ala Ala Pro Pro Arg Gln Pro Asp Lys Glu Phe Cys Phe<br>    325                 330                 335 | 1186 |
| atg gat gag gag gag gaa gat gag atc cga gtt tgaggctgga ccgaaagttg | 1239 |

```
Met Asp Glu Glu Glu Glu Asp Glu Ile Arg Val
    340                 345 aaagtcgcct tcacatctct gggctgcatc ttttccctgc tgctgctgcc gccttctcta    1299
tgacctttga ccttactctg taggtgcagc taagaggctc attggagtag accctggacc    1359
tcagggattg gggtgccaga gaagtaaagt agcaggggca ctggcgcctg gtggcctgac    1419
tctgacctaa ccttccttac cgcaccagcc tgggacggat ccgagcccca gcggaagcc     1479 attctcttcc gggccctttg ctctcagcct ggcctcagat ggatgccaga tgttagtttg    1539
agttgctgcc gcaatggcag ggaagccagg tgtgggcttc tctccaaggt catgacact     1599 tggctccctt ctgttcacct tgtgtctgca gcctacccag agatatatg cagcaggagg     1659 cagggtgct cacgtgtttg agctcctcct tcttccacct ctggctcctc actgaagcct    1719
ggtgttcttt ggggttcagc tgaagccagg ggacagcctc aactattaca ctaaatgcag    1779
cctgtcccag aggctgcatc ccaggacagg atggggcaca aaggaacga acacccctg     1839 cttctagctt cttgggttct caagacacta ggaacaggaa aggggccagc tctgcccatg    1899
ggtgtgtttg ttccttgtta ctatgtttta aacctgaata gagcactgcc aaaatccct    1959 gccaggagac tagtgaccgt cttggtggct gagtgactgt tatctcacct gaatctggtg    2019
tacagaccct gccaggttg gactgtggca ggcagccac caccagtgtt tgtcccggaa     2079
cccccacctc catagctgtt agtggctgaa ggagggctgt gtaagaaaag ttctggaata    2139
cgatgcttaa atgatacatt attccctggg gtgtgagctg cgctttggct agttagtggc    2199
ctctccttgg gctctgggcc aggcctcgca aaaacacaaa acaagatggg actgtatttg    2259
attggaattc cagggttttt ttgttttgttt gttttttggct ttttgggata cggtctcact   2319
ctgtagccca agctggcctc aagctcatag cgagcctccc ttaccctagg agcttcggtt   2379
gcaagtgtgc accactgctc ctggctgttt tgttcttctg aaagctgttt tgctcagctc    2439
ctgtaactct acccagaacg ctagtagagg caggggcctg agccctgggg gtggtagctc    2499
attactttcc tatgctggga gcaggctgac ctgctccctg gtctagcaca gccagtggga    2559
atctggggag agagcaagct agattacaag cagagtctgg ccagatggtg gccagccatg    2619
ggctgctgtg cttccagagg ccaccctcct agattcagac cctgaagtgc tcactgggcc    2679
cctgactggt gctcctacgc aggtaggcag tgactgagct acagagctgt gtctctggcc    2739
agcagtacac acacaacaca cacacacccc tctcctaaat ctacctggtt ggttctaaac    2799
tctaaacttt gtattttttt ccatgacatt gaaaaagcag taagaaaaca ttaaaatttc    2859
ctcctaaca                                                             2868

<210> SEQ ID NO 5
<211> LENGTH: 349
<212> TYPE: PRT
<213> ORGANISM: Mus musculus

<400> SEQUENCE: 5

Met Pro Ile Leu Lys Gln Leu Val Ser Ser Val Asn Ser Lys Arg
  1               5                  10                  15

Arg Ser Arg Ala Asp Leu Thr Ala Glu Met Ile Ser Ala Pro Leu Gly
              20                  25                  30

Asp Phe Arg His Thr Met His Val Gly Arg Ala Gly Asp Ala Phe Gly
          35                  40                  45

Asp Thr Ser Phe Leu Thr Ser Lys Ala Arg Glu Ala Asp Asp Glu Ser
      50                  55                  60
```

-continued

```
Leu Asp Glu Gln Ala Ser Ala Ser Lys Leu Ser Leu Ser Arg Lys
 65                  70                  75                  80

Phe Arg Gly Ser Lys Arg Ser Gln Ser Val Thr Arg Gly Asp Arg Glu
                 85                  90                  95

Gln Arg Asp Met Leu Gly Ser Leu Arg Asp Ser Ala Leu Phe Val Lys
            100                 105                 110

Asn Ala Met Ser Leu Pro Gln Leu Asn Glu Lys Glu Ala Ala Glu Lys
            115                 120                 125

Asp Ser Ser Lys Leu Pro Lys Ser Leu Ser Ser Pro Val Lys Lys
130                 135                 140

Ala Asp Ala Arg Asp Gly Gly Pro Lys Ser Pro His Arg Asn Gly Ala
145                 150                 155                 160

Thr Gly Pro Asn Ser Pro Asp Pro Leu Leu Asp Glu Gln Ala Phe Gly
                165                 170                 175

Asp Leu Met Asp Leu Pro Ile Met Pro Lys Val Ser Tyr Gly Leu Lys
            180                 185                 190

His Ala Glu Ser Ile Leu Ser Phe His Ile Asp Leu Gly Pro Ser Met
            195                 200                 205

Leu Gly Asp Val Leu Ser Ile Met Asp Lys Asp Gln Trp Gly Ser Glu
210                 215                 220

Glu Glu Glu Glu Ala Gly Gly Tyr Arg Asp Lys Glu Gly Pro Ser Ser
225                 230                 235                 240

Ile Val Gln Ala Pro Pro Val Leu Glu Val Val Pro Pro Leu Gly Arg
                245                 250                 255

Gln Glu Ser Lys Ala Ser Trp Asp Gln Ala Ser Met Leu Pro Pro His
            260                 265                 270

Ala Val Glu Asp Asp Gly Trp Ala Val Ala Pro Ser Pro Ser Ser
            275                 280                 285

Ala Arg Ser Val Gly Ser His Thr Thr Arg Asp Ser Ser Ser Leu Ser
290                 295                 300

Ser Tyr Thr Ser Gly Val Leu Glu Glu Arg Ser Pro Ala Phe Arg Gly
305                 310                 315                 320

Pro Asp Arg Val Ala Ala Ala Pro Pro Arg Gln Pro Asp Lys Glu Phe
                325                 330                 335

Cys Phe Met Asp Glu Glu Glu Asp Glu Ile Arg Val
            340                 345
```

```
<210> SEQ ID NO 6
<211> LENGTH: 16
<212> TYPE: PRT
<213> ORGANISM: Artificial Sequence
<220> FEATURE:
<223> OTHER INFORMATION: Consensus CRIB motif (Bubelo, PD et al.,
      J.Biol.Chem. 270:29071-29074, p. 29073, 1995)
<221> NAME/KEY: VARIANT
<222> LOCATION: (1)...(16)
<223> OTHER INFORMATION: Xaa = Any Amino Acid

<400> SEQUENCE: 6

Ile Ser Xaa Pro Xaa Xaa Xaa Xaa Phe Xaa His Xaa Xaa His Val Gly
 1               5                  10                  15

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide primer ZC18859
```

```
<400> SEQUENCE: 7
ggggcagcaa gcggtcac                                            18

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide primer ZC18860

<400> SEQUENCE: 8
tccgcggcct ccttctca                                            18

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer ZC19115

<400> SEQUENCE: 9
tgcccaagag cctgtcgtcc                                          20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer ZC19119

<400> SEQUENCE: 10
ctggctgtgc tagaccaggg                                          20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer ZC19190

<400> SEQUENCE: 11
acggtcacta gtctcctggc                                          20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer ZC19191

<400> SEQUENCE: 12
gctttcagag gcccagacag                                          20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer ZC19192

<400> SEQUENCE: 13
tcgtcaagga gtgggtcagg                                          20

<210> SEQ ID NO 14
<211> LENGTH: 20
```

```
<212> TYPE: DNA
<213> ORGANISM: Artificial Sequence
<220> FEATURE:
<223> OTHER INFORMATION: Oligonucleotide primer ZC19193

<400> SEQUENCE: 14
gatacggtct cactctgtag                                               20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer ZC19278

<400> SEQUENCE: 15
acagagtaag gtcaaaggtc                                               20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer ZC19270

<400> SEQUENCE: 16
aggctgcatc ccaggacagg                                               20

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer ZC6768

<400> SEQUENCE: 17
gcaattaacc ctcactaaag ggaac                                         25

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer ZC694

<400> SEQUENCE: 18
taatacgact cactataggg                                               20

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide primer ZC19514

<400> SEQUENCE: 19
gcgcgcggcc ggccaccatg cccattctca aa                                 32

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide primer ZC19515

<400> SEQUENCE: 20
```

```
gcgcgcggcg cgcctcaaac tcggatctca tc                          32

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide primer ZC18489

<400> SEQUENCE: 21
tcatcgccat ggtaaccac                                         19

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer ZC18106

<400> SEQUENCE: 22
aaacgcagtc tcctgtccag                                        20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer ZC18438

<400> SEQUENCE: 23
gcatttgagc tcaaacctcc                                        20

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer ZC18165

<400> SEQUENCE: 24
aagcatgcgg agtccatcat g                                      21

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer ZC18214

<400> SEQUENCE: 25
tgctgtctca agacagccag                                        20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer ZC18275

<400> SEQUENCE: 26
ttagtgcaca tgctcgcagc                                        20

<210> SEQ ID NO 27
<211> LENGTH: 21
<212> TYPE: DNA
<213> ORGANISM: Artificial Sequence
```

```
<220> FEATURE:
<223> OTHER INFORMATION: Oligonucleotide primer ZC18213

<400> SEQUENCE: 27
tattctgcac tggccttcct c                                              21

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide primer ZC18285

<400> SEQUENCE: 28
tggcctcaaa tggatgccag                                                20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer ZC18388

<400> SEQUENCE: 29
tgttaatagg tctgcctcag                                                20

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide primer ZC18105

<400> SEQUENCE: 30
agtcaacctc agggctcata c                                              21

<210> SEQ ID NO 31
<211> LENGTH: 19
<212> TYPE: DNA
<213> ORGANISM: Artificial Sequence
<220> FEATURE:
<223> OTHER INFORMATION: Oligonucleotide primer ZC18452

<400> SEQUENCE: 31
agagtgctga gttaaacgc                                                 19
```